(12) United States Patent
Jennings et al.

(10) Patent No.: US 9,360,425 B2
(45) Date of Patent: Jun. 7, 2016

(54) METHOD FOR CHARACTERIZING THE STABILITY OF FOULANTS AND/OR EFFICACY OF FOULANT INHIBITORS WITHIN PETROLEUM-BASED FLUIDS

(71) Applicant: BAKER HUGHES INCORPORATED, Houston, TX (US)

(72) Inventors: David Wayne Jennings, Houston, TX (US); Robert Cable, Missouri City, TX (US); Geoffrey Charles Leonard, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 20 days.

(21) Appl. No.: 14/267,635

(22) Filed: May 1, 2014

(65) Prior Publication Data
US 2014/0326886 A1 Nov. 6, 2014

Related U.S. Application Data

(60) Provisional application No. 61/818,792, filed on May 2, 2013.

(51) Int. Cl.
*G01N 21/59* (2006.01)
(52) U.S. Cl.
CPC ..................................... *G01N 21/59* (2013.01)
(58) Field of Classification Search
CPC ................................ G01N 21/59; G01N 33/26
See application file for complete search history.

(56) References Cited

U.S. PATENT DOCUMENTS

| | | | |
|---|---|---|---|
| 4,390,412 A * | 6/1983 | Dvoracek et al. | 208/48 AA |
| 4,843,247 A | 6/1989 | Yamazoe et al. | |
| 4,846,957 A | 7/1989 | Johnson et al. | |
| 5,420,040 A | 5/1995 | Anfindsen et al. | |
| 5,715,046 A | 2/1998 | Tolvanen et al. | |
| 6,087,662 A | 7/2000 | Wilt et al. | |
| 6,839,137 B2 | 1/2005 | Mason et al. | |
| 6,841,779 B1 * | 1/2005 | Roehner et al. | 250/339.07 |
| 7,067,811 B2 | 6/2006 | Long et al. | |
| 2004/0040464 A1 * | 3/2004 | Andrievsky | C09D 11/328 106/31.49 |
| 2015/0102224 A1 | 4/2015 | Respini | |

FOREIGN PATENT DOCUMENTS

| | | |
|---|---|---|
| EP | 1021710 B1 | 9/2006 |
| WO | 2013192611 A1 | 12/2013 |

OTHER PUBLICATIONS

Bouts, M.N., et al., "An Evaluation of New Asphaltene Inhibitors: Laboratory Study and Field Testing," SPE-28991, pp. 782-787 (Sep. 1995).
MacMillan, D.J., et al., "A Unified Approach to Asphaltene Precipitation: Laboratory Measurement and Modeling," SPE-28990, pp. 788-793 (Sep. 1995).
Carrier, H., et al., "Acoustic method for measuring asphaltene flocculation in crude oils," Jnl of Petroleum Science and Engrg, 27, pp. 111-117 (2000).
Yen, Andrew et al., "Evaluating Asphaltene Inhibitors: Laboratory Tests and Field Studies," SPE 65376, 7 pp. (Feb. 2001).
Asomaning, Samuel, "Test Methods for Determining Asphaltene Stability in Crude Oils," Petroleum Science & Technology, vol. 21, Nos. 3 & 4, pp. 581-590 (2003).
Mousavi-Dehghani, S.A., et al., "An analysis of methods for determination of onsets of asphaltene phase separations," Jnl of Petroleum Science and Engrg. 42, pp. 145-156 (2004).
ASTM D 7061-04, "Standard Test Method for Measuring n-Heptane Induced Phase Separation of Asphaltene-Containing Heavy Fuel Oils as Separability Number by an Optical Scanning Device," 5 pp. (date unknown).
Squicciarini, Michael et al., "Characterization of the Chemical Properties of Crude Oils to Explain Observed Asphaltene Inhibitor Specificity," SPE-106209, 6 pp. (2007).

* cited by examiner

*Primary Examiner* — David Porta
*Assistant Examiner* — Faye Boosalis
(74) *Attorney, Agent, or Firm* — Mossman, Kumar & Tyler, P.C.

(57) ABSTRACT

A petroleum-based fluid sample may be centrifuged in a centrifuge vial where a light may be passed through the petroleum-based fluid sample to identify an amount of transmitted light at two or more time intervals. The stability of the foulant(s) and/or efficacy of the foulant inhibitors to prevent the destabilization of the foulants may be determined by comparing a change in the amounts of transmitted light through the petroleum-based fluid sample. The petroleum-based fluid sample may include a petroleum-based fluid, at least one foulant, and an optional additive for destabilizing the foulant(s). The additive may be or include a first component, such as but not limited to n-alkanes, iso-alkanes, alkenes, alkynes, cyclo-alkanes, natural gas, natural gas condensate, alcohols, ethers, ketones, organic acids, acetates, carbon dioxide, and combinations thereof.

20 Claims, 15 Drawing Sheets

METHOD FOR CHARACTERIZING THE STABILITY OF FOULANTS AND/OR EFFICACY OF FOULANT INHIBITORS WITHIN PETROLEUM-BASED FLUIDS

TECHNICAL FIELD

The present invention relates to a method for characterizing the instability of foulants and/or efficacy of foulant inhibitors within petroleum-based fluids. The method involves centrifuging a petroleum-based fluid sample having at least one foulant, while passing light through the petroleum-based fluid sample to compare a change in an amount of transmitted light at two or more time intervals for determining the stability of foulants and/or efficacy of foulant inhibitors within the petroleum-based fluid.

BACKGROUND

Various types of foulants pose problems during production and refining of hydrocarbon fluids. Foulants are materials within the production fluid that may become destabilized and agglomerate to each other and deposit on equipment, which can cause problems with the fluid during extraction, transporting, processing, refining, combustion, and the like. Examples of foulants include asphaltenes, iron sulfide, coke, ores, clays, waxes, hydrates, naphthenates, and the like.

Asphaltenes are most commonly defined as that portion of petroleum, which is insoluble in heptane. Asphaltenes exist in crude oil as both soluble species and in the form of colloidal dispersions stabilized by other components in the crude oil. Asphaltenes may include a distribution of thousands of chemical species having chemical similarities, although by no means nearly all identical. In general, asphaltenes have higher molecular weights and are the more polar fractions of crude oil, and can precipitate upon pressure, temperature, and compositional changes in crude oil resulting from blending or other mechanical or physicochemical processing. Asphaltene precipitation and deposition can cause problems in subterranean reservoirs, upstream production facilities, mid-stream transportation facilities, refineries, and fuel blending operations. In petroleum production facilities, asphaltene precipitation and deposition can occur in near-wellbore reservoir regions, wells, flowlines, separators, and other equipment. Once deposited, asphaltenes present numerous problems for crude oil producers. For example, asphaltene deposits can plug downhole tubulars, wellbores, choke off pipes and interfere with the functioning of safety shut-off valves, and separator equipment. Asphaltenes have caused problems in refinery processes such as desalters, distillation preheat units, and cokers.

Many formation fluids, such as petroleum fluids, contain a large number of components with very complex compositions. For the purposes herein, a formation fluid is the product from a crude oil well at the time the fluid is produced until it is refined. Some of the potentially fouling-causing components present in a formation fluid, for example wax and asphaltenes, are generally stable in the crude oil under equilibrium reservoir conditions, but may aggregate or deposit as temperatures, pressures, and overall fluid compositions change as the crude oil is removed from the reservoir during production. Waxes comprise predominantly high molecular weight paraffinic hydrocarbons, i.e. alkanes. Asphaltenes are typically dark brown to black-colored amorphous solids with complex structures and relatively high molecular weights.

In addition to carbon and hydrogen in the composition, asphaltenes also may contain nitrogen, oxygen and sulfur species, and may also contain metal species such as nickel, vanadium, and iron. Typical asphaltenes are known to have different solubilities in the formation fluid itself or in certain solvents like carbon disulfide or aromatic solvents, such as benzene, toluene, xylene, and the like. However, the asphaltenes are insoluble in solvents like paraffinic compounds, including but not limited to pentane, heptane, octane, etc. Asphaltene stability can even be disturbed by mixing petroleum-based fluids, such as crude oils, shale oils, condensates, and other types of formation fluids, of different origins at certain ratios as the chemistry of the petroleum-based fluids from different sources may be incompatible and induce destabilization of the foulants therein.

When the formation fluid from a subsurface formation comes into contact with a pipe, a valve, or other production equipment of a wellbore, or when there is a decrease in temperature, pressure, or change of other conditions, foulants may precipitate or separate out of a well stream or the formation fluid, while the formation fluid is flowing into and through the wellbore to the wellhead. While any foulant separation or precipitation is undesirable in and by itself, it is much worse to allow the foulant precipitants to accumulate and deposit on equipment in the wellbore. Any foulant precipitants depositing on wellbore surfaces may narrow pipes and clog wellbore perforations, various flow valves, and other wellsite and downhole locations. This may result in wellsite equipment failures and/or closure of a well. It may also slow down, reduce or even totally prevent the flow of formation fluid into the wellbore and/or out of the wellhead.

Similarly, undetected precipitations and accumulations of foulants in a pipeline for transferring crude oil could result in loss of crude oil flow and/or equipment failure. Crude oil storage facilities could have maintenance or capacity problems if foulant precipitations occur. These fluids also carry unstable foulants into the refinery, as well as possibly into finished fuels and products where the foulants cause similar problems for facilities of this nature.

Accordingly, there are large incentives to mitigate fouling during refining. There are large costs associated with shutting down production units because of the fouling components within, as well as the cost to clean the units. The foulants may create an insulating effect within the production unit, reduce the efficiency and/or reactivity, and the like. In either case, reducing the amount of fouling would reduce the cost to produce hydrocarbon fluids and the products derived therefrom.

One technique to reduce the adverse effects of foulants within the formation fluid is to add a foulant inhibitor to the petroleum-based fluid having potential fouling causing components. A 'foulant inhibitor' is defined herein to mean an inhibitor that targets a specific foulant. Several foulant inhibitors may be added to reduce the adverse effects of each type of foulant, e.g. asphaltene foulant inhibitors, paraffin foulant inhibitors, and iron sulfide foulant inhibitors all may be added to the fluid to decrease the adverse effects of each type of foulant, such as deposition, accumulation, and/or agglomeration of the foulant(s). However, it has been difficult to analyze the stability or efficacy of the foulant inhibitors because the experimental conditions may not always represent actual 'field' conditions of the formation fluid.

One such analytical technique available for measuring the stability of the foulants before and after treatment with foulant inhibitors is the ASTM D7601-04 method and minor variations thereof (hereinafter referred to as the 'ASTM method'), and is well known by those skilled in the art. To perform this technique, a fluid sample is placed into a Turbiscan™ measurement device where the Turbiscan™ sends photons into the sample where the photons are scattered many times by objects in suspension, such as droplets, solid particles, bubbles, etc. After scattering, the photons emerge from the fluid sample and are detected by the Turbiscan™ measurement device. The Turbiscan™ measurement device utilizes a mobile reading head having a NIR diode and two detectors, which are the transmission detector and backscattering detector. No mechanical or other external stress in excess of gravitational force, i.e. equivalent to about 1×g relative centrifugal force (RCF), is added to the fluid sample. The Turbiscan™ Heavy Fuel model was specifically developed to analyze asphaltene stability in heavy fuel oil (HFO) for use with the ASTM method.

The parameters of the ASTM method using the Turbiscan™ measurement device may include a concentration of petroleum fluid that is about 1 vol % to about 10 vol %, a foulant inhibitor concentration of about 10 ppm to about 3000 ppm, and a destabilizing agent of about 90 vol % to about 99 vol %. The sample volume is 5-8 mL. The wavelength of the light is passed through the sample at 850 nm, and the pathlength of the vial is about 12 mm. The RCF is 1×g, and the temperature of the fluid during the procedure is ambient.

Another analytical technique available for measuring the stability of asphaltene foulants before and after treatment with asphaltene foulant inhibitors is the heptane precipitation test, which uses a near infrared light probe to detect the percent transmittance through the petroleum-based fluid and heptane mixture; this method is well known by those skilled in the art (hereinafter referred to as the 'heptane precipitation method'). To perform this technique, a petroleum-based fluid(s) and the destabilizing additive (heptane) are mixed in a tube to form the fluid sample. The sample remains upright for one hour to allow asphaltene foulant molecules to flocculate and settle and/or interact with asphaltene foulant inhibitors.

The procedure may apply an optional centrifugal force to the sample after the equilibration step for a period of time. After the settling time and the optional centrifugation the percent transmittance from a light source having a wavelength of 830 nm collimated light is measured with a colorimeter probe that is dipped into the upper third of the centrifugation tube. As asphaltene foulant constituents become destabilized, these molecules aggregate and settle to the bottom of the centrifugation tube. During this process, the light transmission through the sample at the upper third of the tube may increase and therefore indicate destabilization of asphaltene foulants. In addition, the volumetric amount of the precipitated asphaltenes may be quantified by visually reading the amount of solids relative to the centrifuge tube volumetric hash marks.

By calculating the % dispersive power of foulant inhibitors with the heptane precipitation method, the efficacies of different asphaltene foulant inhibitors per petroleum-based fluid may be compared. The % Dispersion afforded by an asphaltene foulant inhibitor during a heptane precipitation test having a low transmittance and high "% Dispersion" are indications of good inhibition against asphaltene foulant precipitation.

The parameters of the method using the heptane precipitation method may include a concentration of petroleum fluid that is about 1 vol % to about 10 vol %, an asphaltene foulant inhibitor concentration of about 10 ppm to about 3000 ppm, and a destabilizing additive of about 90 vol % to about 99 vol %. The sample volume is 8-12 mL. The wavelength of the light is passed through the sample at 830 nm, and the pathlength of the centrifuge vial is 20 mm.

However, there are several shortcomings when measuring foulant stability and/or efficacy of a foulant inhibitor to improve foulant stability with the Turbiscan™ or colorimeter that are discussed in more detail below. Thus, it would be desirable to develop better methods of analyzing the stability of the foulants and/or foulant inhibitors.

SUMMARY

There is provided, in one form, a method for determining the stability of at least one foulant within a petroleum-based fluid. A petroleum-based fluid sample is centrifuged in a centrifuge vial where the petroleum-based fluid sample includes a petroleum-based fluid, at least one foulant, and an optional additive in an effective amount for destabilizing the foulant(s). The additive may include a first component that may be or include, but is not limited to, n-alkanes, iso-alkanes, alkenes, alkynes, natural gas, natural gas condensate, alcohols, ethers, ketones, organic acids, acetates, and combinations thereof. A light may be passed through the petroleum-based fluid sample to identify an amount of transmitted light at two or more time intervals for determining the stability of the foulant(s) by comparing a change in transmitted light.

There is further provided in an alternative non-limiting embodiment of the method where the petroleum-based fluid may be or include a crude oil, a production fluid, natural gas condensate, shale oil, shale gas condensate, bitumen, diluted bitumen (dil-bit), refinery fractions, finished fuel, finished petroleum products, and combinations thereof. Diluted bitumen is defined herein to mean a blend made from heavy crudes and/or bitumens having a diluent where the density of the diluent included in the blend is less than about 800 kg/m$^3$. The petroleum-based fluid sample may be centrifuged at about the same time the light is passed through the petroleum-based fluid sample. 'About the same time' is defined herein to be where the centrifugation and the passing the light through the sample occur less than 30 minutes apart from one another, alternatively, less than 5 minutes apart from one another, or where the process of centrifugation and the passing the light through the petroleum sample overlap in a non-limiting embodiment but each process does not necessarily start and stop at the same time.

In another non-limiting embodiment, the method may determine the stability of at least one foulant with at least one foulant inhibitor, and combinations thereof within the petroleum-based fluid sample. To do this, the petroleum-based fluid sample must include at least one foulant inhibitor in addition to the other petroleum-based fluid sample components described above. The foulant(s) within the petroleum-based fluid may be or include, but are not limited to, asphaltenes, iron sulfide, waxes, coke, sand, ores, clays, hydrates, naphthenates, and combinations thereof. The amount of the petroleum-based fluid within the petroleum-based fluid sample may range from about 1 vol % to about 100 vol %.

Measuring the change in transmitted light through the petroleum-based fluid sample at two or more time intervals may correlate to the stability of at least one foulant alone or in the presence of at least one foulant inhibitor within the petroleum-based fluid sample.

DETAILED DESCRIPTION

Figure 1:
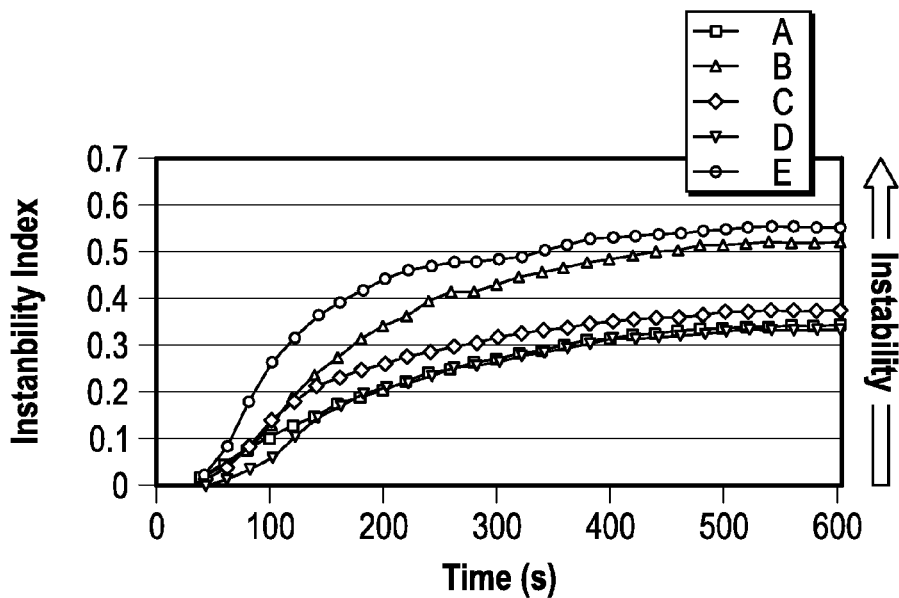
FIG. 1 is a graph illustrating the instability index changing over time for a crude oil with foulant inhibitor products A-E.
Figure 2:
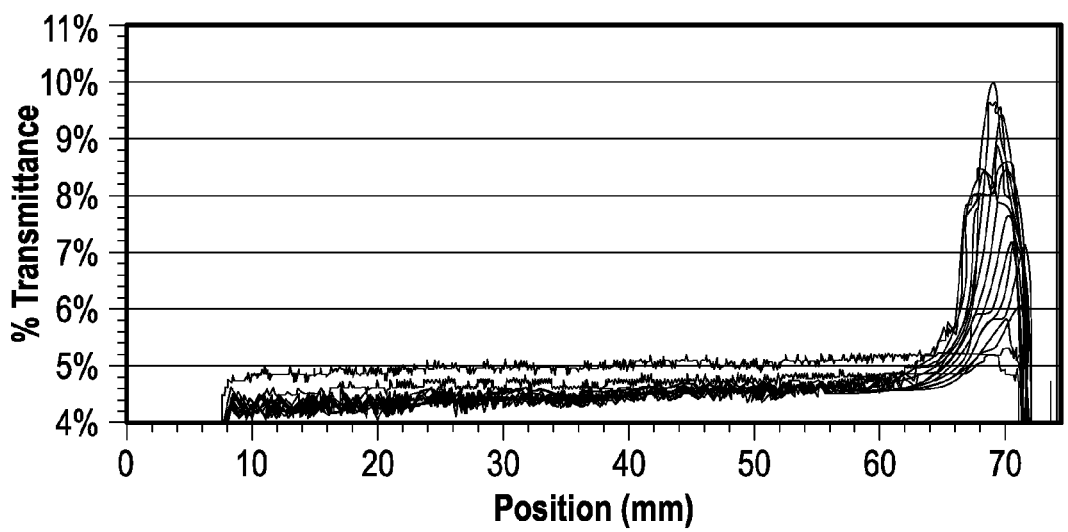
FIG. 2 illustrates the analysis of a crude oil with foulant inhibitor product A by using the ASTM method where the amount of transmittance is measured along the length of the vial.
Figure 3:
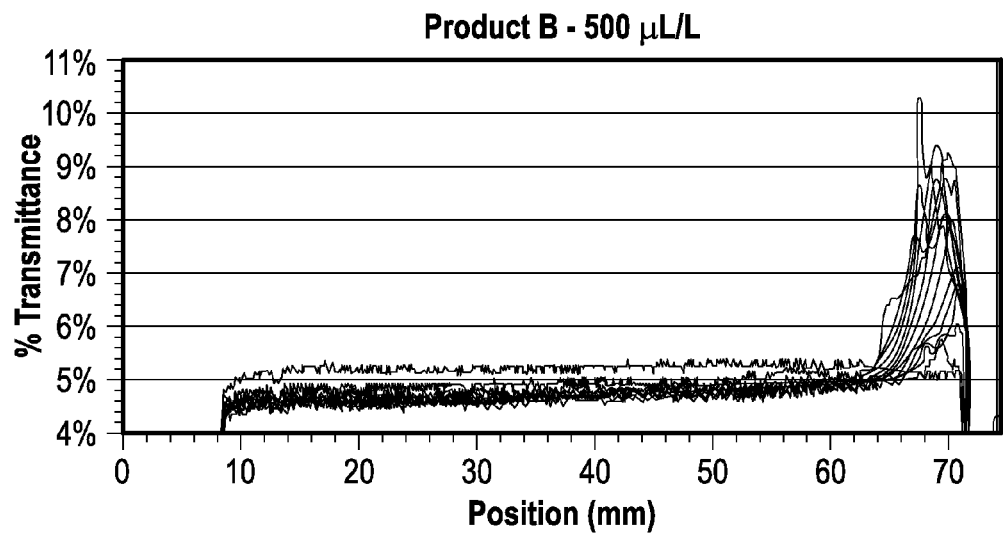
FIG. 3 illustrates the analysis of a crude oil with foulant inhibitor product B by using the ASTM method where the amount of transmittance is measured along the length of the vial.
Figure 4:
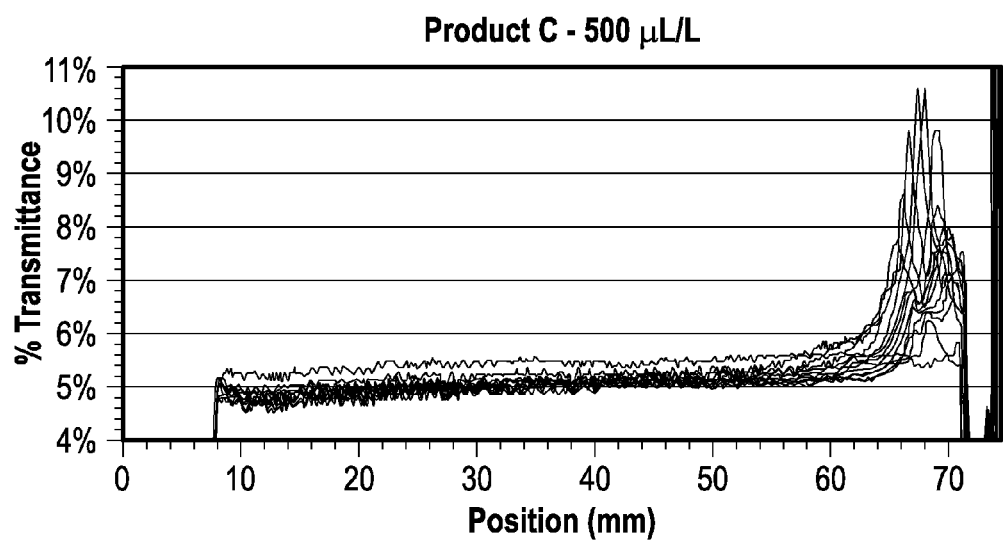
FIG. 4 illustrates the analysis of a crude oil with foulant inhibitor product C by using the ASTM method where the amount of transmittance is measured along the length of the vial.
Figure 5:
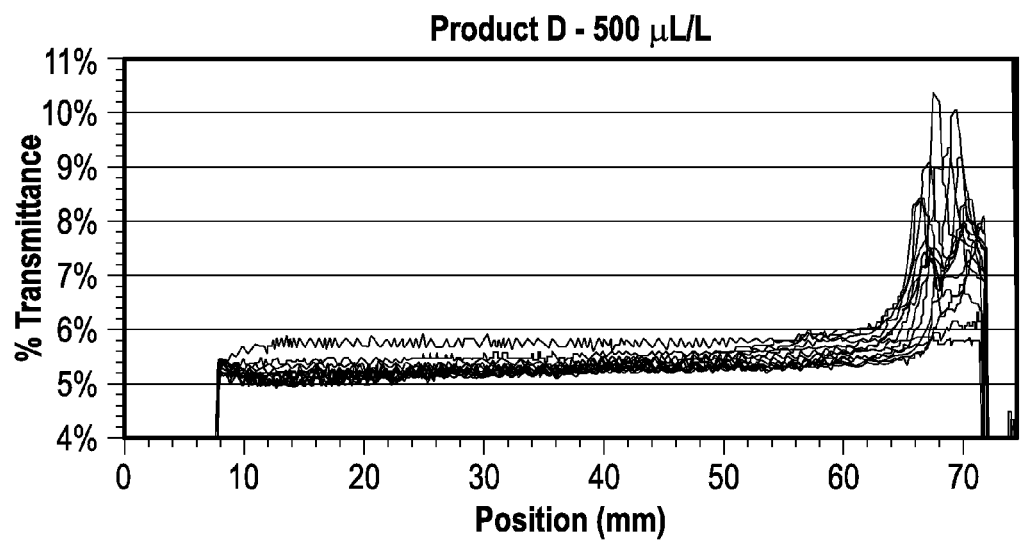
FIG. 5 illustrates the analysis of a crude oil with foulant inhibitor product D by using the ASTM method where the amount of transmittance is measured along the length of the vial.
Figure 6:
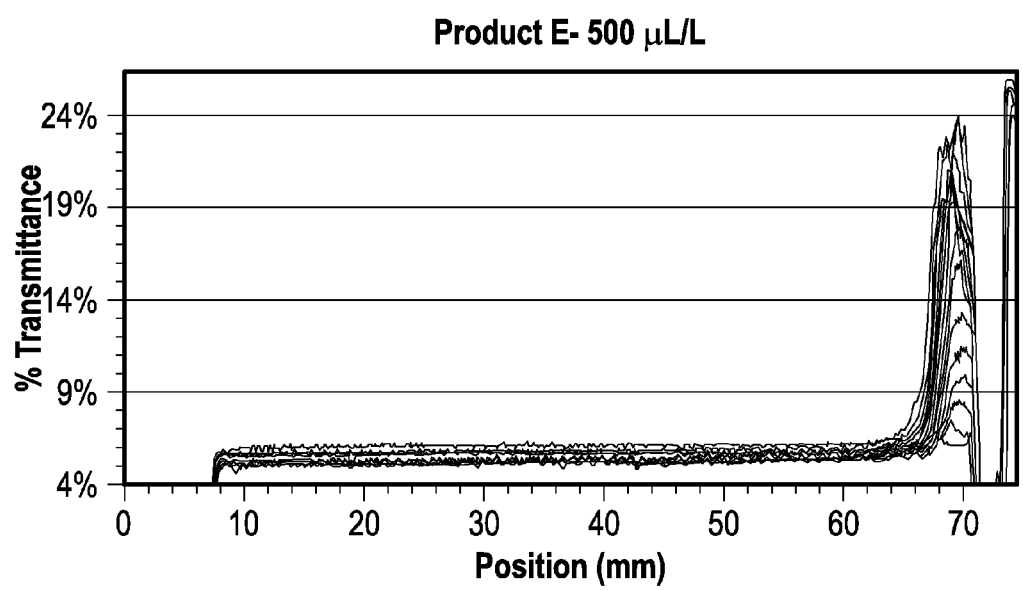
FIG. 6 illustrates the analysis of a crude oil with foulant inhibitor product E by using the ASTM method where the amount of transmittance is measured along the length of the vial.
Figure 7:
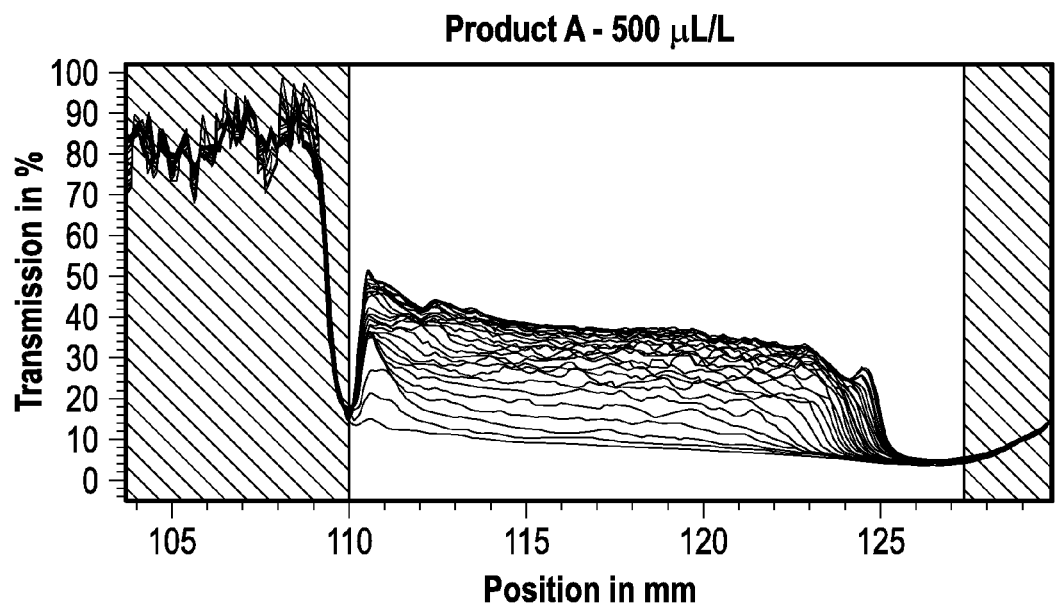
FIG. 7 illustrates the analysis of a crude oil with foulant inhibitor product A by using the method described herein where the amount of transmittance is measured along the length of the vial.
Figure 8:
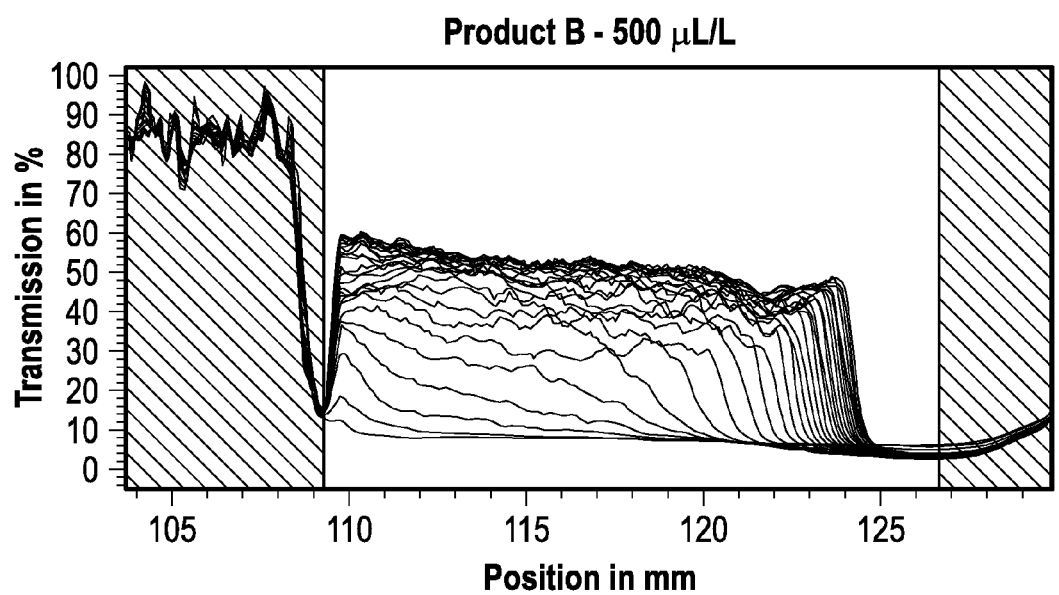
FIG. 8 illustrates the analysis of a crude oil with foulant inhibitor product B by using the method described herein where the amount of transmittance is measured along the length of the vial.
Figure 9:
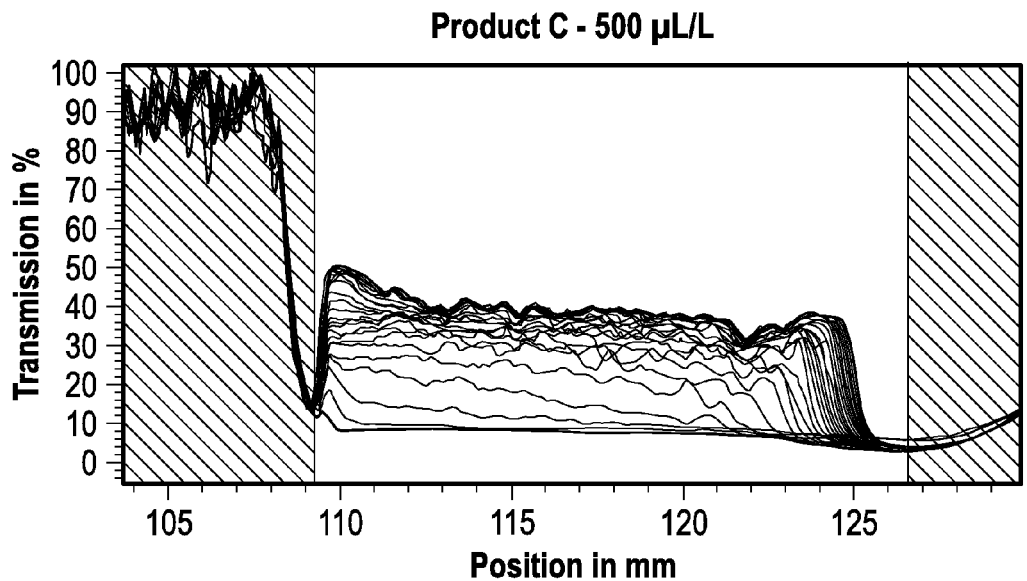
FIG. 9 illustrates the analysis of a crude oil with foulant inhibitor product C by using the method described herein where the amount of transmittance is measured along the length of the vial.
Figure 10:
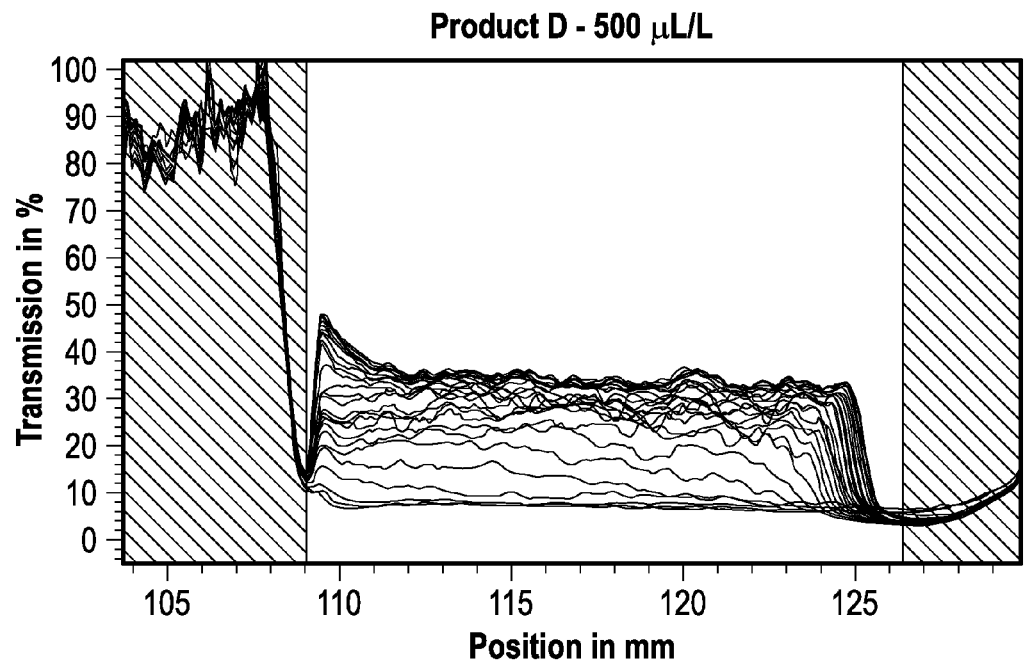
FIG. 10 illustrates the analysis of a crude oil with foulant inhibitor product D by using the method described herein where the amount of transmittance is measured along the length of the vial.
Figure 11:
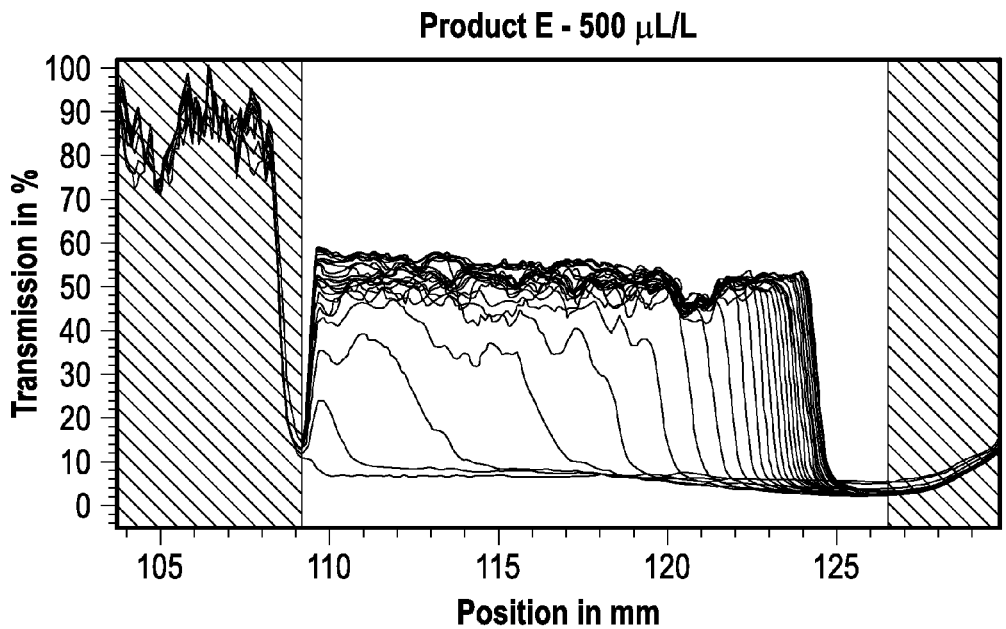
FIG. 11 illustrates the analysis of a crude oil with foulant inhibitor product E by using the method described herein where the amount of transmittance is measured along the length of the vial.

A method has been discovered to determine the stability of foulants and/or efficacy of foulant inhibitors within a petroleum-based fluid sample by centrifuging the petroleum-based fluid sample in a centrifuge vial and passing a light through the petroleum-based fluid sample, hereinafter referred to as the analytical centrifuge stability analysis (ACSA) to distinguish from the ASTM and heptane precipitation methods. In one non-limiting embodiment, the petroleum-based fluid sample may be centrifuged, and a light may be passed through the entire length of the petroleum-based fluid sample at about the same time. A 'petroleum-based fluid sample' is defined herein to be the amount of contents within a centrifuge vial to be used with the methods described.

The stability of the foulant(s) and/or efficacy of foulant inhibitor(s) may be determined from a change in the measured amounts of transmitted light, such that the petroleum-based fluid sample may become cloudier (less transparent) or clearer (more transparent), etc. As foulants are destabilized and flocculated, the changes in the transmitted light may be observed along the centrifuge vial. These changes may be related to the separation or stability of foulant species, foulant species treated with inhibitors, or both. Typically, as foulants precipitate and/or separate, the transmittance increases in the upper regions of the centrifuge vial as destabilized foulants travel to the bottom of the centrifuge vial. 'Upper region' is defined herein to mean the region of the centrifuge vial closest to the centrifuge axis of rotation.

Analysis testing of petroleum-based fluid samples with foulant inhibitors may be used to gauge the efficacy of the foulant inhibitors to improve foulant stability in petroleum-based fluids. 'Foulant stability' is defined herein to mean that a stable foulant is a foulant that either remains in a dispersed or soluble form within the petroleum-based fluid sample, or the foulant precipitates in a less amount and/or at a slower rate. The foulant inhibitor may increase the foulant stability by causing a higher percentage of the foulant to remain in a dispersed or soluble form or reduces the amount and/or rate of foulant precipitation as compared to an identical fluid sample with the foulant in the absence of the foulant inhibitor. A wider range of petroleum-based fluid samples and/or sample conditions may be analyzed with the method than with currently accepted industry methods, such as the ASTM method. Better differentiation of foulant inhibitor performance may be obtained. Better differentiation of foulant inhibitor performance allows selection and development of better performing products for treating industry production and refining problems.

The LUMiSizer™ analytical centrifuge sold by LUM Americas is a non-limiting example of an analytical centrifuge that may be used to centrifuge the petroleum-based fluid sample, while also passing the light through the petroleum-based fluid sample at about the same time. Using the LUMiSizer™ also allows a single point of the analyte to be analyzed, but its main strength is analysis of all of the contents within the centrifuge vial. By analyzing the sample along at least a majority of the centrifuge vial over time, the kinetic mechanisms of the foulants and/or foulant inhibitors may also be measured and analyzed.

The centrifuge vial plays an important role in the amount of light transmitted through the petroleum-based fluid sample. In non-limiting embodiments, the centrifuge vial may have a path length ranging from about 0.1 mm independently to about 10 mm, or from about 1 mm independently to about 4 mm in another non-limiting embodiment. As used herein with respect to a range, "independently" means that any threshold may be used together with another threshold to give a suitable alternative range, e.g. about 0.1 mm independently to about 1 mm is also considered a suitable alternative range.

The light source may emit light having a wavelength ranging from about 370 nm independently to about 2500 nm, or alternatively from about 470 nm independently to about 1600 nm in another non-limiting embodiment. The amount of transmittance of the light passing through the petroleum-based fluid sample may be measured at two or more time intervals. 'Time interval' is defined as an amount of time between two intervals. Time intervals may vary from about less than about 1 second independently to about 24 hours, or from about 10 seconds independently to about 30 minutes.

These measurements may be taken at a specified location on the centrifuge vial, or the transmittance may be measured along a majority of the centrifuge vial, i.e. about 50% or more of the length of the centrifuge vial. In an alternative embodiment, the transmittance may be measured from the bottom of the centrifuge vial to slightly above the top of the petroleum-base fluid sample or from about 80% to about 100% of the centrifuge vial.

The petroleum-based fluid sample may include, but is not limited to, a petroleum-based fluid, and at least one foulant. In a non-limiting instance, the petroleum-based fluid sample may include a petroleum-based fluid, at least one foulant, an optional additive for destabilizing the foulant(s), and at least one foulant inhibitor. For example, if asphaltene stability is to be analyzed by the method, then a foulant inhibitor targeting asphaltenes may be added to the petroleum-based fluid sample. In another non-limiting embodiment, two or more foulant inhibitors may be added to the petroleum-based fluid sample to analyze stability and possible synergy of a blend or combination of at least two foulant inhibitors.

The petroleum-based fluid may have destabilized foulants present within the fluid. In non-limiting examples, such as during refining or fuel blending, two or more petroleum-based fluids may be mixed together. Sometimes, changes in physical conditions are sufficient to induce destabilization, or even the mixture of different petroleum-based fluids that have incompatible chemistries. Said differently, even if neither petroleum-based fluid, alone, has destabilized foulants or the petroleum-based fluid would not act as a destabilizing additive by itself, the mixing or the mixture of two or more petroleum-based fluids may further destabilize the foulants present in either petroleum-based fluid.

In a non-limiting embodiment, an optional destabilizing additive to destabilize the foulant may be added to the petroleum-based fluid or the petroleum-based fluid sample prior to centrifuging the petroleum-based fluid sample. The destabilizing additive may be added to a petroleum-based fluid to further destabilize any foulants therein. The amount of the additive within the petroleum-based fluid sample ranges from about 0.1 vol % to about 99 vol %, alternatively from about 50 vol % independently to about 95 vol % in another non-limiting embodiment. The additive may include a first component, such as but not limited to, n-alkanes, iso-alkanes, alkenes, alkynes, natural gas, natural gas condensate, alcohols, ethers, ketones, organic acids, acetates, carbon dioxide, cyclo-alkanes, and combinations thereof. The number of carbons within the first component may range from about 1 C independently to about 30 C, or alternatively from about 5 C independently to about 16 C in another non-limiting embodiment.

The additive may include a second component in combination with the first component, such as but not limited to, aromatic compounds, n-alkanes, iso-alkanes, cyclo-alkanes, alkenes, alkynes, natural gas, natural gas condensate, alcohols, ethers, ketones, organic acids, acetates, carbon dioxide, and combinations thereof. The second component, alone, may not destabilize the foulants alone and/or foulants in the presence of foulant inhibitor(s), but the second component may be beneficial when used in combination with the first component for controlling the amount of overall destabilization of the foulants alone and/or foulants in the presence of foulant inhibitor(s). Non-limiting combinations of the first component and the second component within the additive may include an n-alkane with an aromatic alkane, an n-alkane with a cycloalkane, and the like.

In another non-limiting embodiment, the method may be practiced in the presence of other chemicals or materials found in sub-terranian reservoirs, upstream production facilities, mid-stream transportation facilities, refining operations, and fuel blending operations. These chemicals and/or materials include, but are not limited to, water, brine, surfactants, acids, inorganic scale, formation sand, formation clays, corrosion by-products, upstream petroleum production chemicals, and refinery processing chemicals. These chemicals may or may not affect the foulant stability and/or foulant inhibitor efficacy.

The petroleum-based fluid may be or include at least one fluid, such as but not limited to, a production fluid, crude oil, natural gas condensate, shale oil, shale gas condensate, bitumen, diluted bitumen (dil-bit), refinery fractions, finished fuel, finished petroleum products, and combinations thereof. In a non-limiting embodiment, the petroleum-based fluid sample may be only one fluid where determining the stability of the one fluid may be necessary. In an alternative embodiment, the petroleum fluid may be a mixture of at least two fluids to determine how one fluid may affect the stability of foulants within another fluid.

The petroleum-based fluid within the petroleum-based fluid sample may range from about 1 vol % independently to about 100 vol %, alternatively from about 1 vol % independently to about 50 vol %, or from about 5 vol % independently to about 40 vol %. These experimental conditions allow for better resemblance to field conditions than the ASTM method and/or standard heptane precipitation tests when analyzing the stability of foulants and/or efficacy of foulant inhibitors to increase the foulant stability. The described method may analyze the petroleum-based fluid sample by destabilizing only a selected fraction of the foulants, so only the most unstable foulants would precipitate and more closely represent field deposition conditions.

The temperature of the petroleum-based fluid sample may range from about 4 C independently to about 200 C, or alternatively from about 20 C independently to about 150 C, or from about 25 C independently to about 100 C in another non-limiting embodiment. The foulant(s) within the petroleum-based fluid sample may range from about 0.1 wt % independently to about 30 wt %, or alternatively from about 0.5 wt % independently to about 10 wt %. The foulants may be or include, but are not limited to, asphaltenes, iron sulfides, waxes, coke, sand, ores, clays, hydrates, naphthenates, and combinations thereof. Non-limiting examples of asphaltene foulant inhibitors that may be tested with this method include alkylphenol polymers, alkylphenol-formaldehyde copolymers, alkylbenzene sulfonic acids, olefin-maleic anhydride copolymers, polyisobutylene succinic anhydride copolymers, and derivatives and combinations thereof.

The invention will be further described with respect to the following Examples, which are not meant to limit the invention, but rather to further illustrate the various embodiments.

EXAMPLES

Example 1

Example 1 Compared the ACSA Method Invention to the ASTM Method and Heptane Precipitation Test.

Crude oil from Mississippi was treated with asphaltene foulant inhibitor products A-E and destabilized by the addition of a specified amount of heptane, and asphaltene stability was evaluated by an ASTM D7601-04-type method, the heptane precipitation method, and the ACSA method described herein using a LUMiSizer™ analytical centrifuge for comparison of the results from each method. Results are shown in Table 1 and FIGS. 1-11.

The ASTM method analyzes asphaltene stability by qualitative observation of transmittance traces and calculation of a separability number parameter, which is listed next to each product in Table 1. The separability number indicates the ability of the asphaltene foulant alone, and/or asphaltene foulant in the presence of asphaltene foulant inhibitor(s), to separate from the petroleum-based fluid sample. For the ASTM method tests, each of the petroleum-based fluid samples had 1.4 vol % of oil with 500 ppm of asphaltene foulant inhibitor concentration (Products A-E), and 98.6 vol % of destabilizing additive; the overall sample volume was 7 mL in the vial. The crude oil with asphaltene foulant inhibitor Product E had the highest separability number, while the crude oil with foulant inhibitor Product C had the lowest separability number.

The heptane precipitation test used a colorimeter to analyze asphaltene stability by calculating a percent dispersion, which is listed next to each product in Table 1. The % Dispersion indicates the amount of product dispersed within the petroleum-based fluid sample. The crude oil with asphaltene foulant inhibitor Product B had the highest % Dispersion, while the crude oil with asphaltene foulant inhibitor Product A had the lowest % Dispersion. For the heptane precipitation tests, each of the petroleum-based fluid samples had 1.0 vol % of oil with 500 ppm of asphaltene foulant inhibitor concentration (Products A-E), and 99 vol % of destabilizing additive; the overall sample volume was 10 mL in the centrifuge vial. The wavelength used was 830 nm, the pathlength of the vial was 20 mm, the RCF applied prior to analysis with the light probe was approximately 180×g, and the temperature was 25 C. The crude oil was diluted with heptane (the destabilizer additive) to destabilize asphaltene foulants therein.

The ACSA method analyzes asphaltene stability by calculating an instability index, which is also listed next to each product in Table 1. The instability index indicates the degree of instability for the asphaltene foulant and is measured by calculating the difference in transmittance over a certain period of time and normalizing the results to the theoretical maximum transmittance. The lower the instability index, the more stable the fluid. The instability index ranges from 0-1.0 with a value of zero indicating no instability. FIG. 1 is a graph illustrating the instability index changing over time for the crude oil treated with asphaltene foulant inhibitor Products A-E. As noted by the graph, the crude oil with asphaltene foulant inhibitor Product E had the highest instability index, while the crude oils with asphaltene foulant inhibitor Products A and D had the lowest instability index. Note in addition to the final instability index value, differences in the kinetic or rate of change within the instability index may be determined as another indicator of asphaltene stability and/or asphaltene inhibitor efficacy.

TABLE 1

Separability Number, % Dispersion, and Instability Index for Crude Oil Treated with Asphaltene Foulant Inhibitor Products A-E and Destabilizing Additive Heptane

| Sample | Turbiscan Separability Number | Colorimeter % Dispersion | LUMiSizer Instability Index |
|---|---|---|---|
| Crude Oil, Untreated | 8.10% | 0 | 0.5338 |
| Product A - 500 µL/L | 0.16% | 43.16 | 0.3408 |
| Product B - 500 µL/L | 0.15% | 62.52 | 0.5189 |
| Product C - 500 µL/L | 0.12% | 57.30 | 0.3759 |
| Product D - 500 µL/L | 0.13% | 46.24 | 0.3328 |
| Product E - 500 µL/L | 0.20% | 59.75 | 0.5534 |

Turbiscan Oil: Heptane 1.43% v/v; 1 scan per minute
Colorimeter Oil: Heptane 1.0% v/v; 1 scan post 1 hr. settling period and 5 min. of centrifugation (~180 × g RCF)
LUMiSizer Oil: Heptane 7.5% v/v; 1 scan per 0.33 minute, 200 rpm/5.3 × g (RCF)

The ASTM Method

FIGS. 2-6 illustrate the transmittance traces from the analyses of crude oil treated with asphaltene foulant inhibitor Products A-E, respectively, by the ASTM/Turbiscan™ method. Again, each of petroleum-based fluid samples evaluated with Products A-E had 1.4 vol % of oil with 500 ppm of asphaltene foulant inhibitor concentration (Products A-E), and 98.6 vol % of destabilizing additive; the overall sample volume was 7 mL in the vial. The wavelength used was 850 nm, the pathlength of the vial was 12 mm, no centrifugal force was applied, and the temperature was 25 C. The crude oil was diluted with heptane (the destabilizer additive) to destabilize asphaltenes therein.

In the graphs of FIGS. 2-6, the bottom of the vial is represented by 0 mm on the x-axis, and the meniscus of the liquid is represented by around 70-75 mm on the x-axis. As asphaltenes precipitate and are separated toward the bottom of each vial, the transmittance increased in the upper regions of the vial as represented by FIGS. 2-6. The ASTM/Turbiscan™ method is stationary and does not utilize centrifugation, so it has a slower change in transmittance, and the transmittance changed less. Asphaltene separation and transmittance change was only measurable towards the top of the vial, i.e. from about 60 to 70 mm.

The efficacy of the foulant inhibitor product to increase foulant stability correlates to the change in light transmittance between test samples with and without the product. A lower change in light transmittance relates to better foulant inhibitor performance; said differently, a larger change in transmittance indicates a less effective product. If no foulant inhibitor product is present within the petroleum-based fluid sample, the change in transmittance indicates the relative stability of the foulant alone. When comparing two products, the lowest change in transmittance indicates the best performer amongst asphaltene foulant inhibitor Products A-E. Thus, the best performing product (lowest tendency for asphaltene precipitation), as noted by the separability numbers, was crude oil treated with asphaltene foulant inhibitor Product C, followed by crude oil treated with asphaltene foulant inhibitor Product D. Note as represented by FIGS. 2-6 that very little qualitative difference is present in the ASTM/Turbiscan™ method transmittance traces. Hence, from a qualitative assessment no significant difference could be observed between the sample analyses. In contrast, as will be shown with Example 2, better differentiation is shown with the ACSA method and crude oil treated with asphaltene foulant inhibitor Product D was actually the better performer.

The ACSA Method

FIGS. 7-11 illustrate the transmittance traces from the analyses of crude oil treated with asphaltene foulant inhibitor Products A-E, respectively, by using the ACSA method. Each petroleum-based fluid sample was evaluated with Products A-E, and each sample had 7.5 vol % of oil with 500 ppm of asphaltene inhibitor concentration (Product A-E, respectively), and 92.5 vol % of destabilizer additive; the overall sample volume in the centrifuge vial was 0.4 mL. The wavelength used was 870 nm, the pathlength of the centrifuge vial was 2 mm, the applied RCF was 5.3×g, and the temperature was 25 C.

FIGS. 7-11 display a larger and more noticeable change in transmittance throughout the length of the sample tube over time due to the centrifugal force applied by the LUMiSizer™. The higher concentration of crude oil also affects the testing in that the petroleum-based sample has an increased amount of asphaltene content therein, so it is easier for the destabilized asphaltenes to agglomerate. Hence, it is harder for the asphaltene foulant inhibitor to reduce the destabilization of the asphaltene foulant. Here, around 125 mm on the x-axis represents the bottom of the centrifuge vial. As shown in FIGS. 7-11, solids began to accumulate at the bottom of the centrifuge vial, which translated to a decrease in the percent transmittance over time.

The lowest change in transmittance relates to the efficacy of the product to increase foulant stability; said differently, a larger change in transmittance indicates a less effective product. If no foulant inhibitor product is present within the petroleum-based fluid sample, the change in transmittance indicates the relative stability of the foulant alone or in the presence of a destabilizing additive. When comparing two foulant inhibitor products, the lowest change in transmittance of crude oil samples treated with foulant inhibitor indicates the best performer amongst Products A-E. FIGS. 7-11 indicate that Product D was actually the best performer, followed by Product A and then Product C, which was not predicted according to the ASTM method using the Turbiscan™.

Example 2

Figure 12:
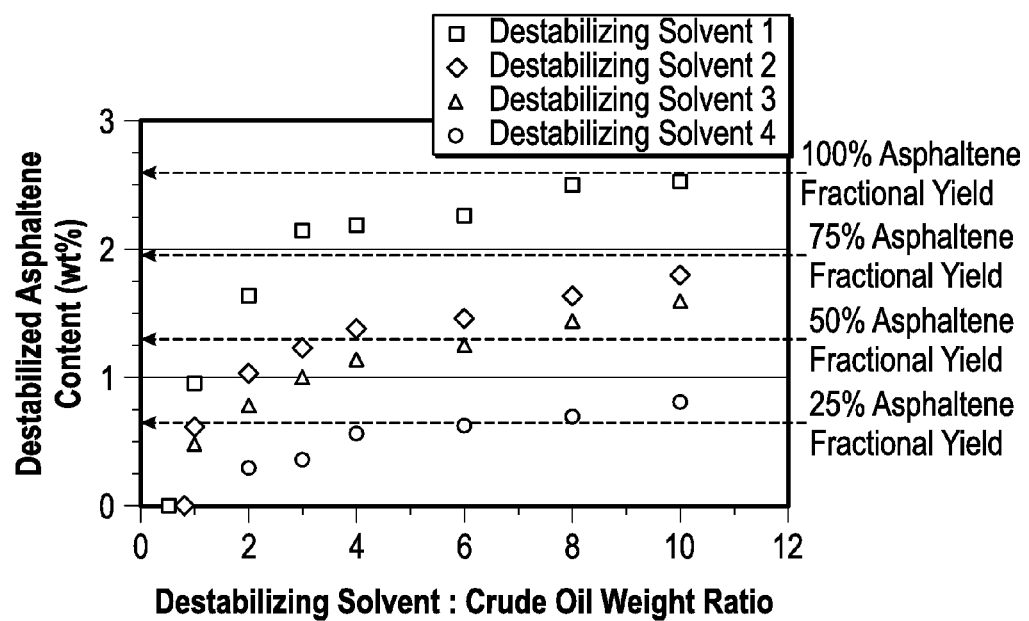
FIG. 12 illustrates the amount of destabilized asphaltene content obtainable using different destabilizing solvents when varying the mixing weight ratios of the destabilizing solvent to the crude oil.

The ACSA method was performed under different destabilizing conditions, such as varied amounts of destabilized foulant. FIG. 12 is a graph depicting the destabilized asphaltene content obtainable based on varying the weight ratio of the amount of destabilizing solvent to the crude oil and varying the destabilizing solvent. Each of samples 1-4 included a crude oil from the Gulf of Mexico, and each sample was mixed with a destabilizing solvent at room temperature (about 21° C.) at various destabilizing solvent to crude oil ratios. Solvent #1 was 100 wt % heptane; solvent #2 was a 75.0 wt % heptane and 25 wt % cyclohexane mixture; solvent #3 was a 67.0 wt % heptane and 33 wt % cyclohexane mixture; solvent #4 was a 50.0 wt % heptane and 50 wt % cyclohexane mixture. The amount of destabilized asphaltenes obtained after approximately 16 hours was measured by using a filtering procedure to collect and weigh the asphaltenes.

Solvent #1 destabilized approximately 100% of the asphaltenes present in the crude oil when the crude oil to heptane weight ratio was above 10. Solvents #2-4 destabilized fewer asphaltenes as the amount of cyclohexane was increased in the solvent mixture. By adjusting the amount of cyclohexane within the destabilizing solvent mixture, different portions of the asphaltene distribution may be studied. Correspondingly, the instability indexes for the ACSA method may vary with different destabilized asphaltene contents, as well as the different chemistries of the asphaltenes present in the sample. Performance of asphaltene inhibitors in the ACSA method will also vary with the different destabilizing solvent and crude oil contents tested.

Figure 13:
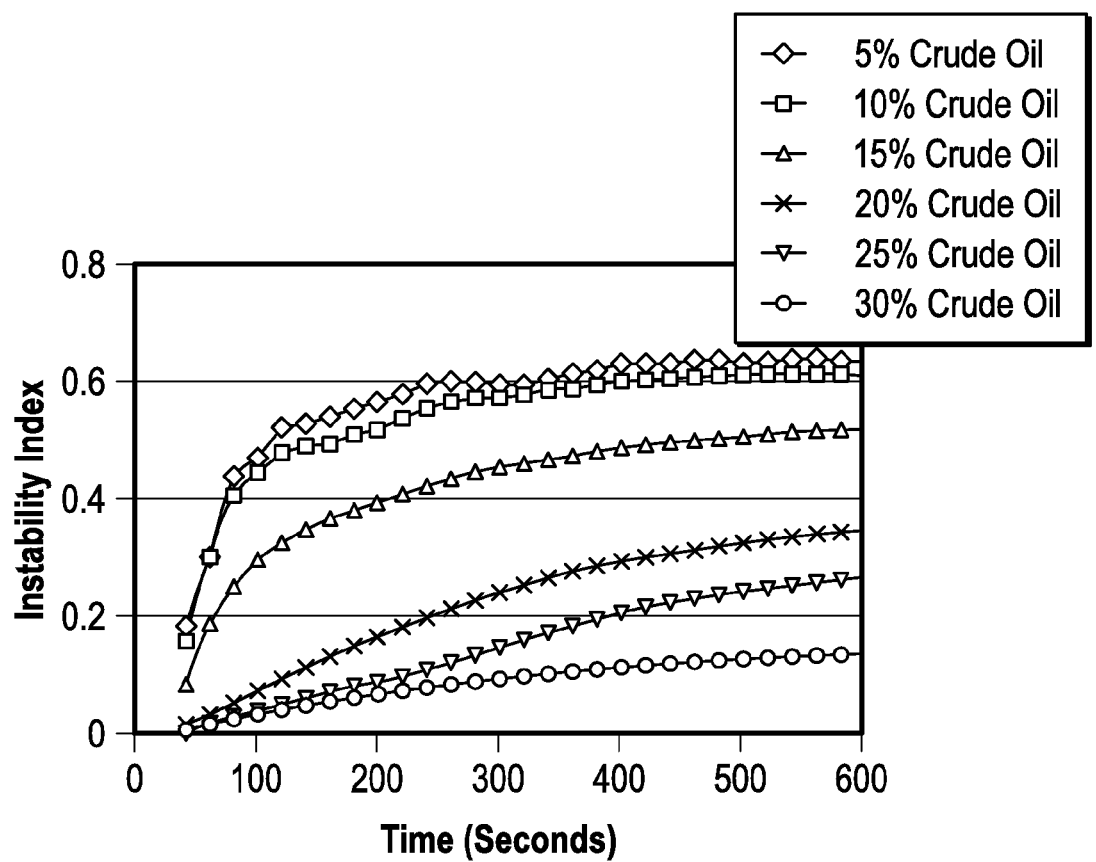
FIG. 13 illustrates the instability index for each sample over a period of time for samples having different amounts of crude oil and destabilizing solvent.
Figure 14A:
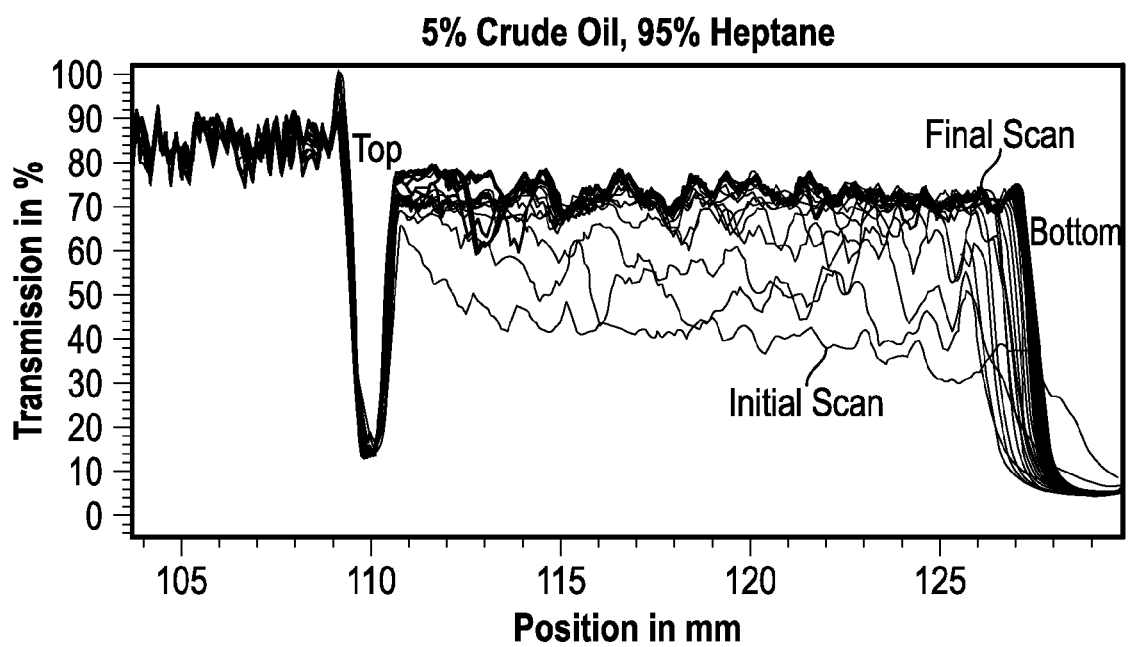
FIGS. 14A-F illustrate the transmittance traces for each sample having different amounts of crude oil and destabilizing solvent over a period of time.
Figure 14B:
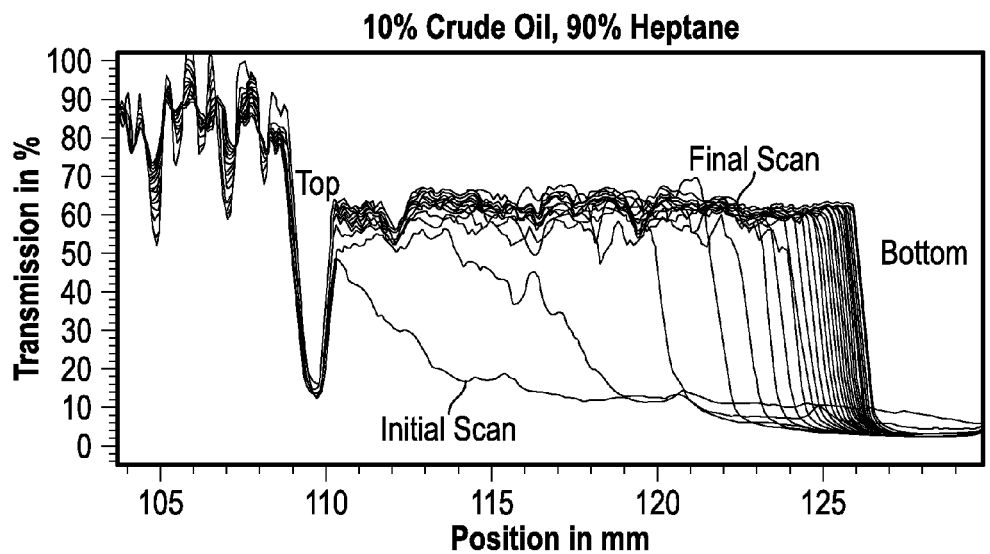
Figure 14C:
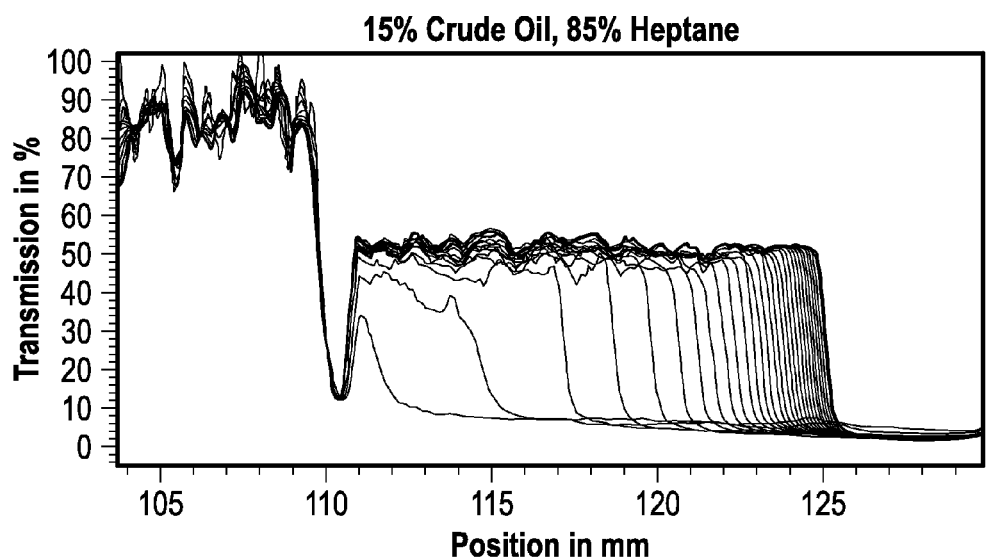
Figure 14D:
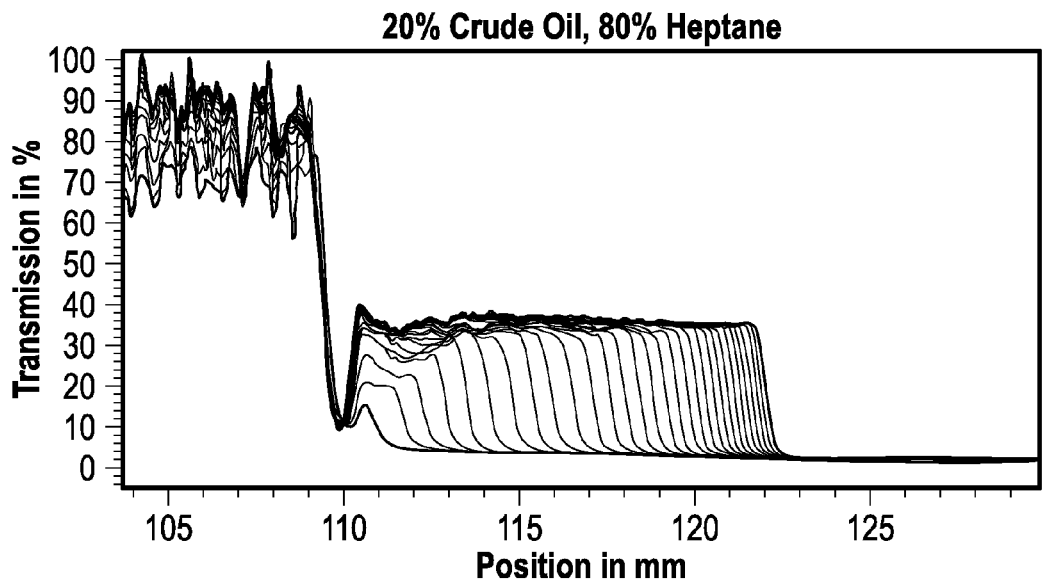
Figure 14E:
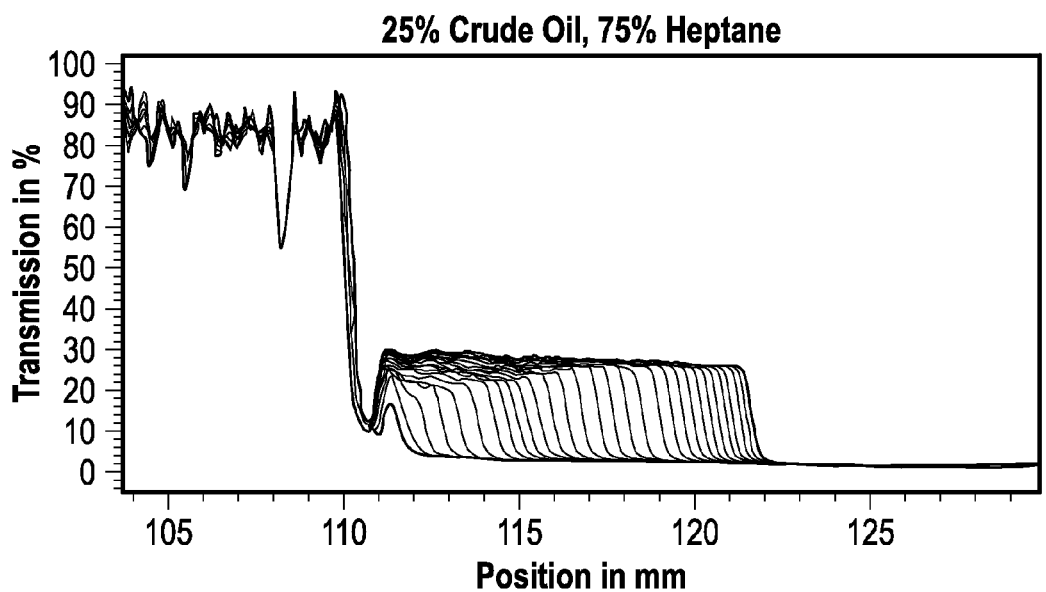
Figure 14F:
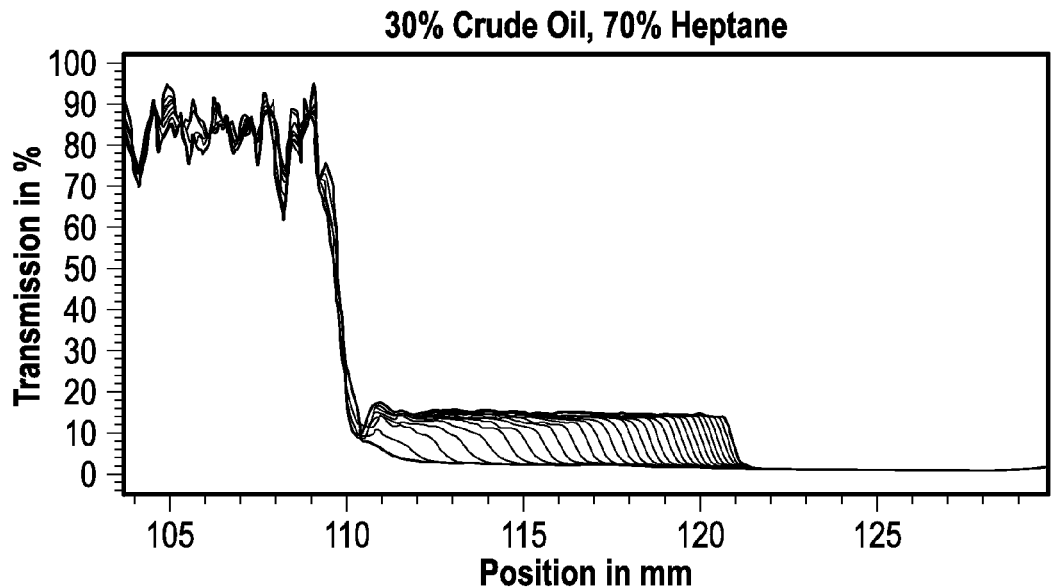

FIG. 13 is a graphical representation illustrating the instability index for each sample over a period of time where each sample had a different amount of crude oil from the Gulf of Mexico and solvent mixture therein. The samples are noted in the graph in terms of the percentage of the crude oil; the 5% crude oil had a 5/95 volume ratio of crude oil to heptane; the 10% crude oil had a 10/90 volume ratio of crude oil to heptane; the 15% crude oil had a 15/85 volume ratio of crude oil to heptane; the 20% crude oil had a 20/80 volume ratio of crude oil to heptane; the 25% crude oil had a 25/75 volume ratio of crude oil to heptane; the 30% crude oil had a 30/70 volume ratio of crude oil to heptane. The measurements were taken using the ACSA method at room temperature and at 200 rpm (5.3×g) for 10 minutes with transmittance scans logged every 20 seconds. FIGS. 14A-F are graphical depictions of the actual transmittance data for each crude oil to heptane ratio. The sample measured in 14A included 5% crude oil and 95% heptane; the sample measured in 14B included 10% crude oil and 90% heptane; the sample measured in 14C included 15% crude oil and 85% heptane; the sample measured in 14D included 20% crude oil and 80% heptane; the sample measured in 14E included 25% crude oil and 75% heptane; and the sample measured in 14F included 30% crude oil and 70% heptane. As depicted in FIGS. 13 and 14A-F, when the sample has less destabilizing solvent, then less asphaltenes are destabilized, and the instability index decreases. The separation kinetics are also slower as shown in FIG. 13.

Figure 15:
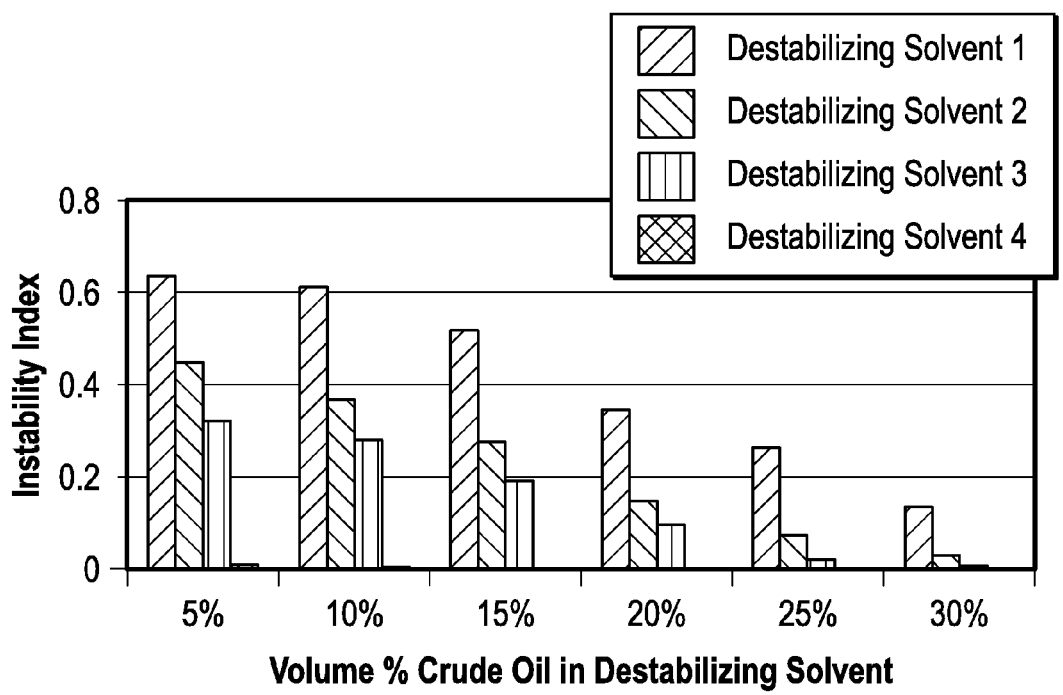
FIG. 15 illustrates the instability index values for each sample set where each sample set includes a different amount of crude oil, and each sample within the sample set includes a different destabilizing solvent.

FIG. 15 shows the final Instability Index at 10 minutes for the same Gulf of Mexico crude oil run at room temperature with all four destabilizing solvents used in FIG. 12 at crude oil/destabilizing solvent volume ratios of 5/95, 10/90, 15/85, 20/80, 25/75, and 30/70. The tests were performed at 200 rpm (5×g) for 10 minutes with transmittance scans logged every 20 seconds. The Instability Index decreases with increasing crude oil volume ratio, and using the weaker destabilizing solvents with increasingly higher cyclohexane content.

Example 3

Figure 16:
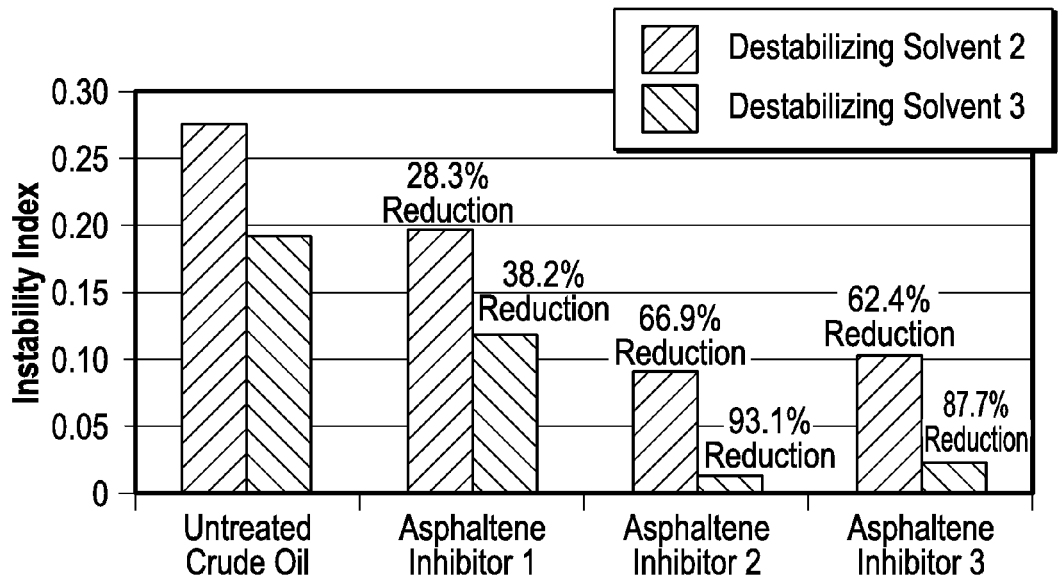
FIG. 16 illustrates the instability index values measured for each sample set where each sample set includes a different asphaltene inhibitor, and where each sample within the set includes a different destabilizing solvent.

FIG. 16 is a graphical representation of the instability index measured using the ACSA method for four sample sets using the Gulf of Mexico crude oil. One sample set used untreated crude oil and the three other sample sets used crude oil treated with different asphaltene inhibitors at a dose rate 300 ppm. A different destabilizing solvent was used for each set. The different destabilizing solvents were compared to determine how the specific destabilizing solvents may affect the performance evaluation of the asphaltene inhibitor within the crude oil. The asphaltene stability in each asphaltene inhibitor treated sample was measured using the ACSA method and compared to the two untreated 'control' samples. Destabilizing solvent #2 was a 75.0 wt % heptane and 25 wt % cyclohexane mixture and destabilizing solvent #3 was a 67.0 wt % heptane and 33 wt % cyclohexane mixture. The ratio of crude oil to destabilizing solvent ratio for each sample was 15 vol % crude oil to 85 vol % destabilizing solvent. The testing occurred at room temperature at 200 rpm (5×g) for 10 minutes with transmittance scans logged every 20 seconds. FIG. 16 shows the final Instability Indexes at 10 minutes.

As noted from FIG. 16, the asphaltene inhibitor treated samples provided a reduction in the instability index over the untreated control samples ranging from 28 to 93% depending on the asphaltene inhibitor and destabilizing solvent used. A higher percentage reduction in the instability index was obtained with destabilizing solvent #3 which destabilizes a lower amount of the asphaltenes present in the crude oil. Note in field operations where asphaltenes become destabilized and deposit in production tubing, the amount of asphaltenes that are destabilized are closer to the amount using destabilizing solvent #3 than destabilizing solvent #2.

Particularly noteworthy in FIG. 16 is the fine differences distinguishable between the performance of Asphaltene Inhibitors #2 and #3. This is typical of the resolution capable in the ACSA method that is not possible with other methods, such as the ASTM method.

Example 4

Figure 17:
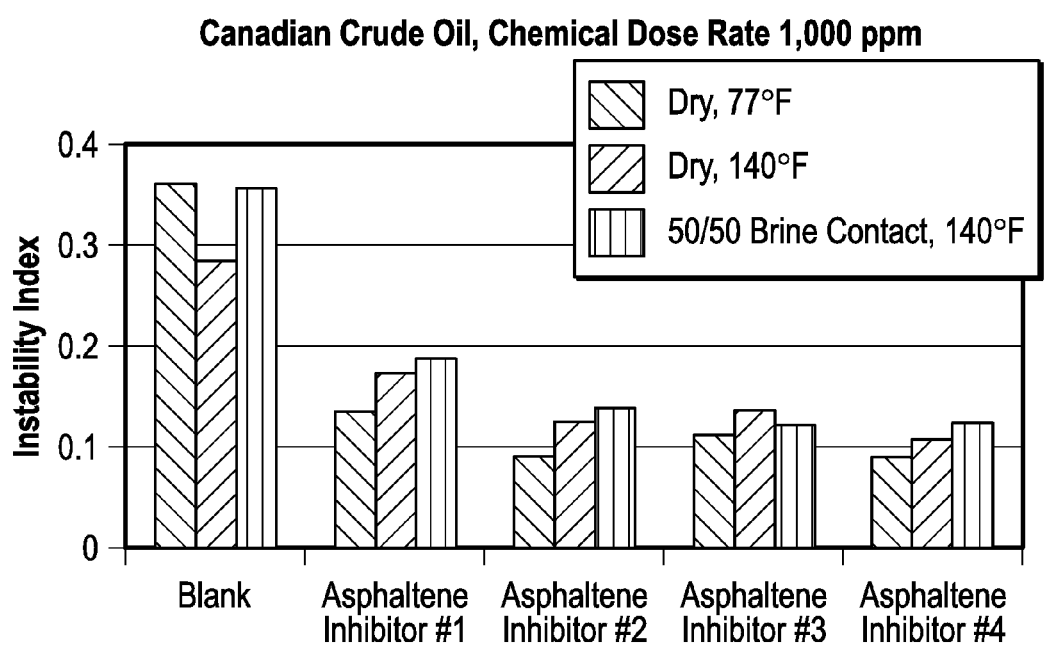
FIG. 17 illustrates the instability index measured for each sample set where each sample set includes a different asphaltene inhibitor, and each sample within the set is subjected to various parameters.
Figure 18:
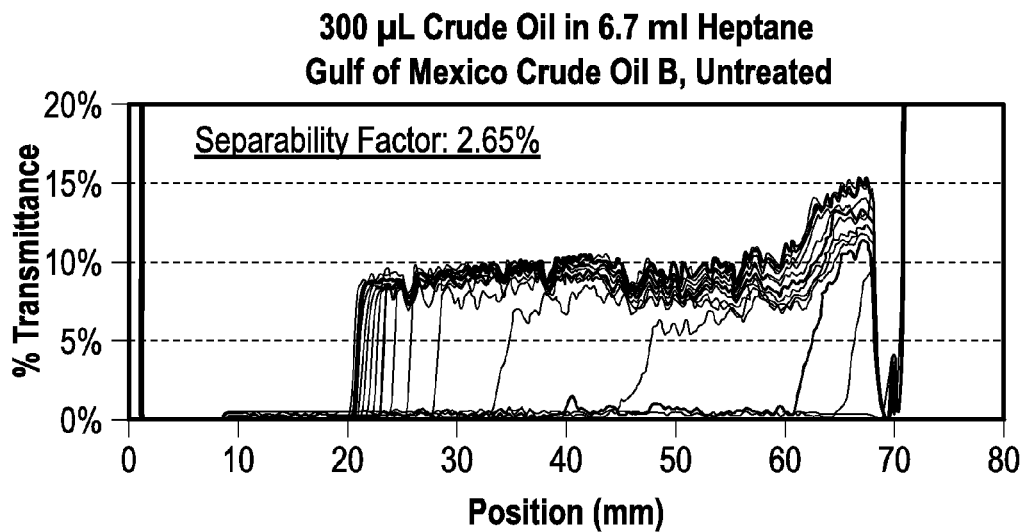
FIGS. 18-21 illustrate the analysis performed with the ASTM/Turbiscan method for a sample with untreated crude oil and samples varying in asphaltene inhibitor dosage.

Five samples of a Canadian crude oil were analyzed under different test conditions. The samples included an untreated or 'control' sample and four samples treated with different asphaltene inhibitors added thereto at 1,000 ppm concentration. Within each sample set, each sample was analyzed with the ACSA method and subjected to conditions, such as 'dry' at 25 C (77 F), 'dry' at 60 C (140 F), and after contacted with a field brine at 60 C. For the brine contact testing, each crude oil sample was mixed at a 50/50 volume ratio with the brine and vigorously shaken and then sat undisturbed for 5 minutes at 60 C to allow the crude oil phase to separate from the brine water phase; the oil phase was then analyzed using the LUMiSizer™ at 60 C. The ACSA method final instability index results from the testing are shown in FIG. 17.

The ACSA method was used to analyze the samples having a crude oil to destabilizing solvent ratio of 20 vol % crude oil to 80 vol % destabilizing solvent. Again, the treated crude oil samples had a 1000 ppm of the particular asphaltene inhibitor. The overall sample volume was 0.4 mL in the centrifuge vial. The destabilizing solvent additive was a 75 wt % heptane and 25 wt % cyclohexane mixture. The wavelength used was 870 nm, the pathlength of the centrifuge vial was 2 mm, and 12×g centrifugal force was applied to each sample. The samples were analyzed at 25 C and 60 C, as designated for each sample within FIG. 17. As noted from FIG. 17, asphaltene inhibitors #2 and #4 were the best performing products at 25 C, asphaltene inhibitor #4 was the best performing product at 60 C without contact from the brine, and asphaltene inhibitors #3 and 4 were the best performing products at 60 C when having contact from the brine. The results in FIG. 17 demonstrate the utility of the LUMiSizer™ method for differentiating asphaltene foulant inhibitor products under variable testing conditions.

Example 5

Samples were analyzed in the presence of and in the absence of an asphaltene foulant inhibitor product at 0 (untreated), 200, 240, and 280 ppm concentrations, respectively. The crude oil in the samples was a Gulf of Mexico crude oil B, which was different from the Gulf of Mexico crude oil mentioned in the previous Examples. The samples were analyzed with the ASTM method in FIGS. 18-21, and the ACSA method in FIGS. 22-25.

The testing carried out by the ASTM/Turbiscan™ method (FIGS. 18-21) analyzed petroleum-based fluid samples having 4.3 vol % of crude oil with 0 (untreated), 200, 240, or 280 ppm of the asphaltene foulant inhibitor in the crude oil and 95.7 vol % of the destabilizing additive; the overall sample volume was 7 mL in the vial. The wavelength used was 850 nm, the pathlength of the vial was 12 mm, no centrifugal force was applied, and the temperature was 25 C. Heptane was the destabilizing additive.

Figure 19:
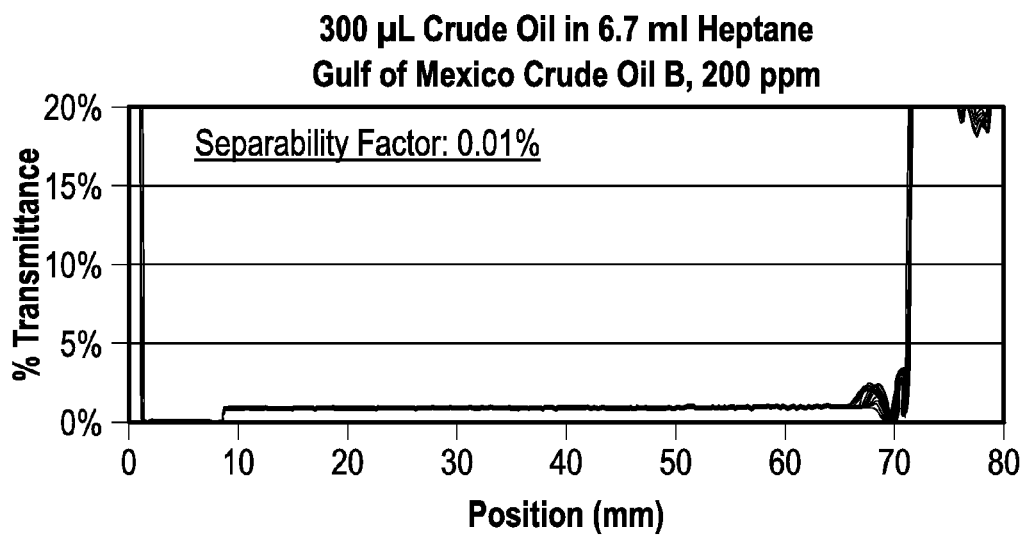
Figure 20:
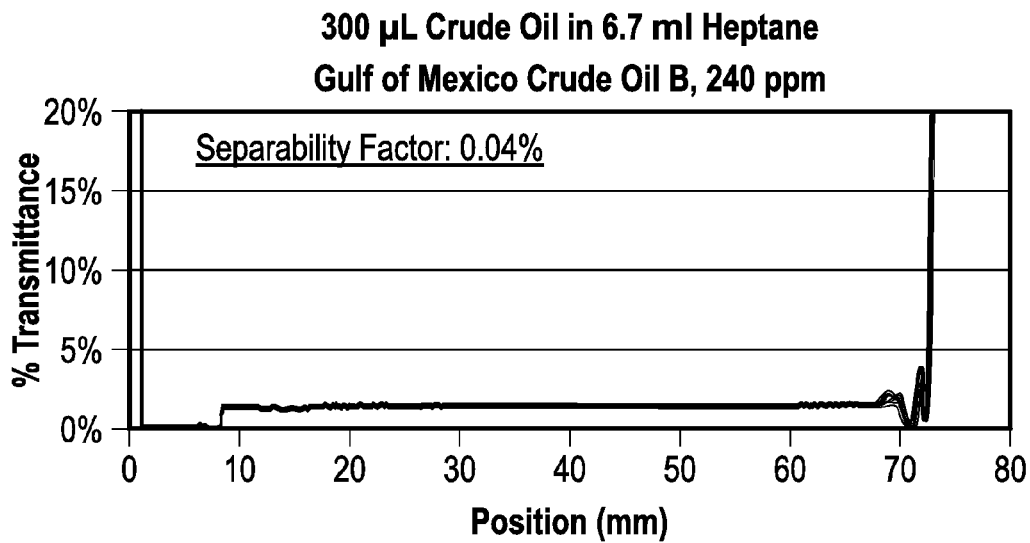
Figure 21:
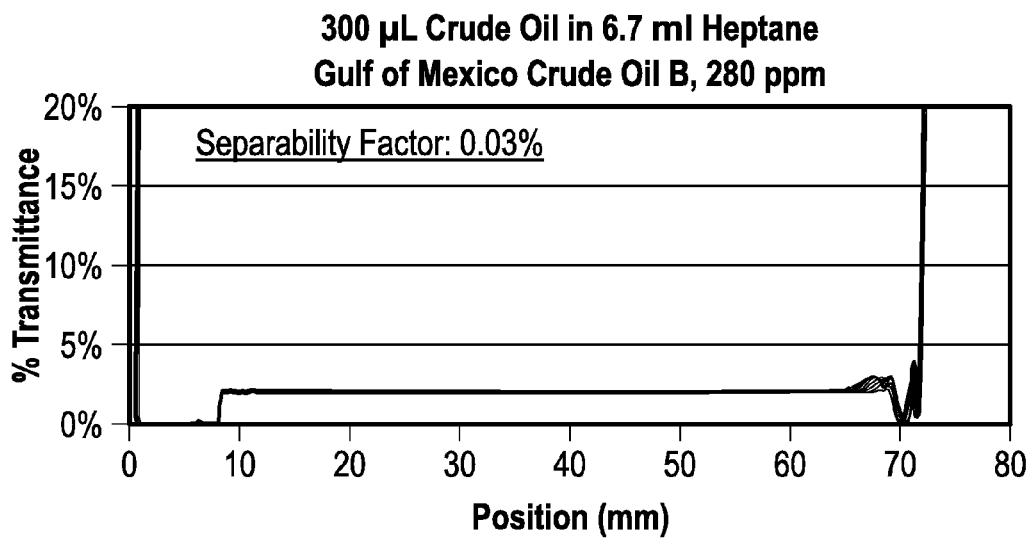
Figure 22:
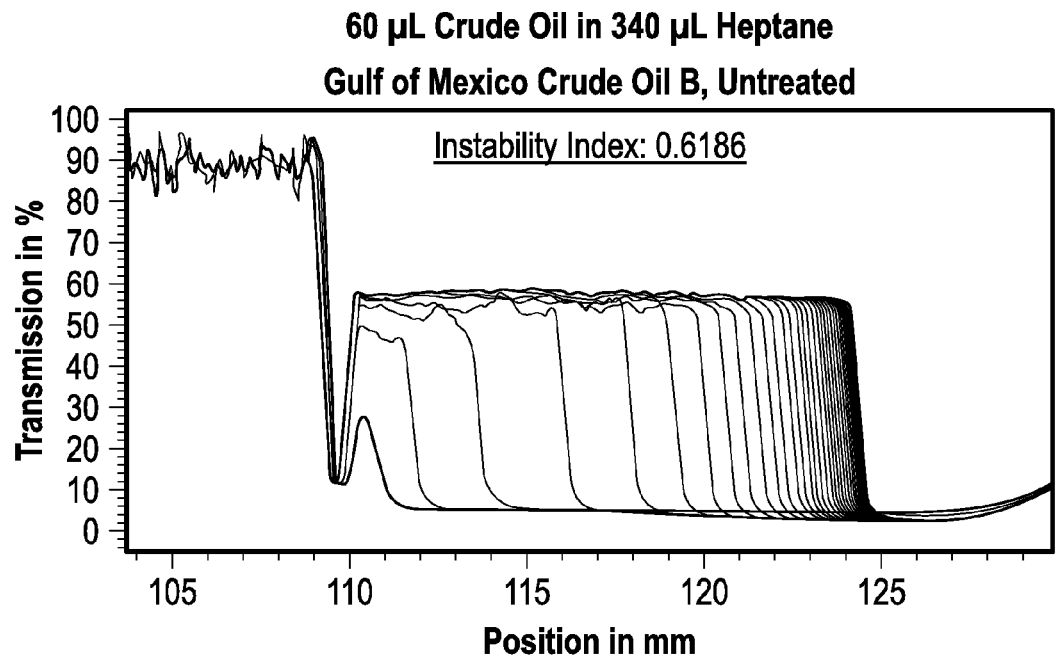
FIGS. 22-25 illustrates the analysis performed with the method described herein for a sample with untreated crude oil and samples varying in asphaltene inhibitor dosage.

The bottom of the sample vial is represented by 8 mm on the x-axis, and the meniscus of the liquid is represented by around 70 mm on the x-axis. As asphaltenes precipitated and are separated by standard gravitational force toward the bottom of each vial, the transmittance increased in the upper regions of the vial. The untreated sample displayed a significant change in transmittance (FIG. 18) throughout the length of the sample vial over the course of the test as destabilized asphaltenes settled to the bottom of the vial. The treated samples displayed very little change in transmittance (FIGS. 19-21). The separability numbers calculated per the ASTM standard protocol indicate no measurable difference between the 200, 240, and 280 ppm dosage amounts.

The testing carried out by the ACSA method (FIGS. 22-25) analyzed petroleum-based fluid samples containing 15 vol % of crude oil with 0 (untreated) 200, 240, or 280 ppm of asphaltene foulant inhibitor in the crude oil and 85 vol % of the destabilizing additive; the overall sample volume was 0.4 mL in the centrifuge vial. The wavelength used was 870 nm, the pathlength of the centrifuge vial was 2 mm, 12×g centrifugal force was applied, and the temperature was 25 C. Heptane was the destabilizing additive.

Figure 23:
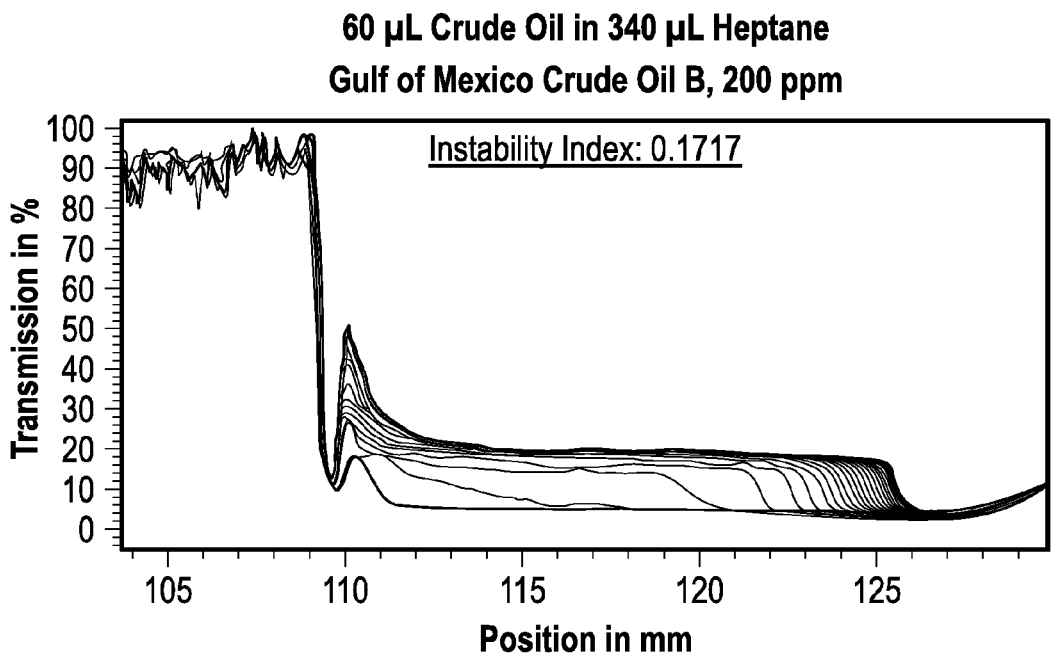
Figure 24:
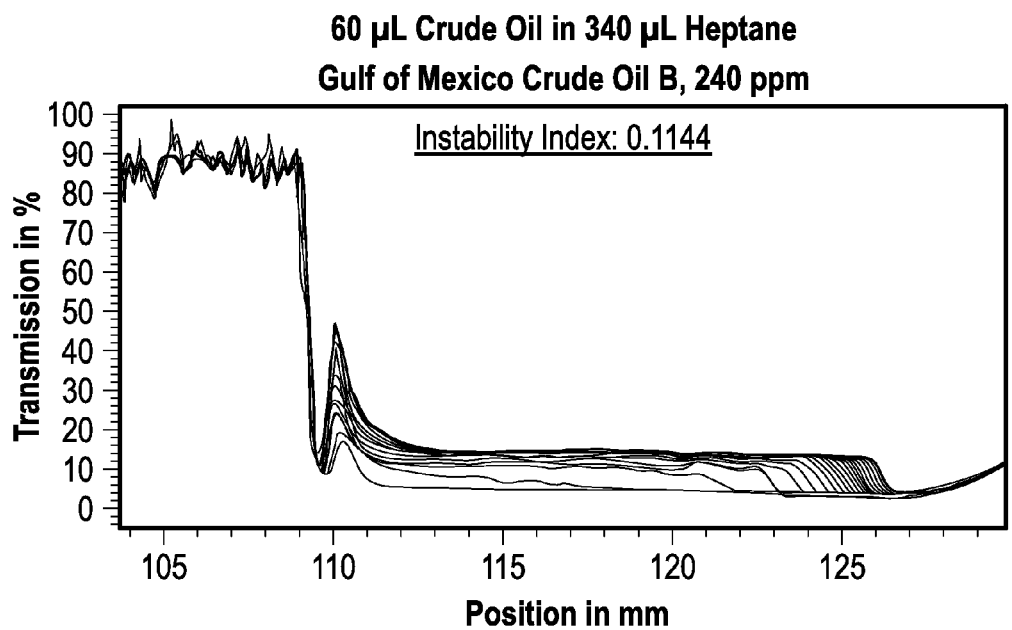
Figure 25:
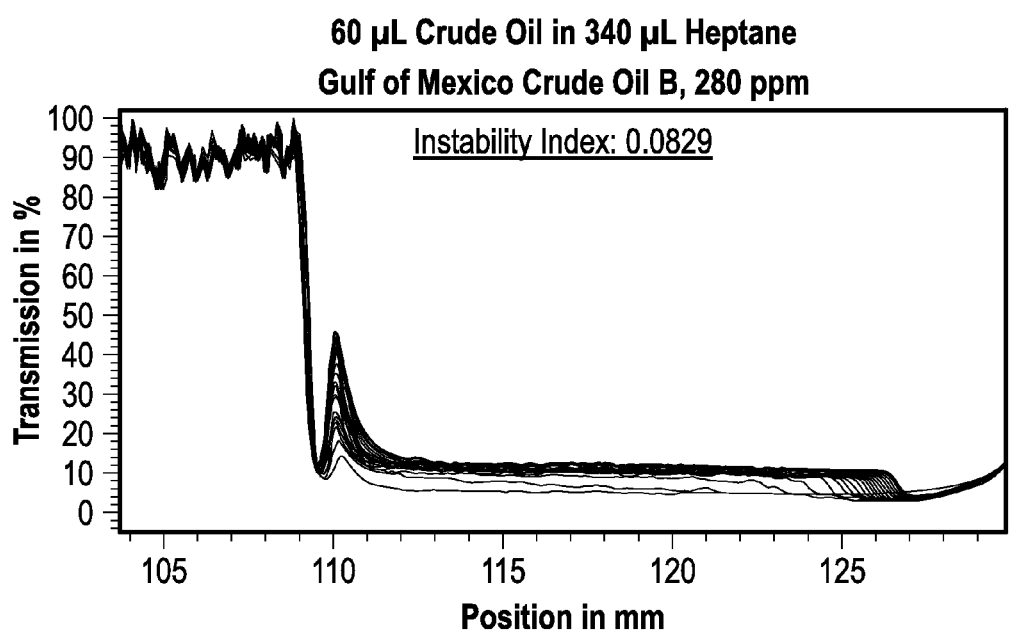

The bottom of the centrifuge vial is represented by 130 mm on the x-axis, and the meniscus of the liquid is represented by around 110 mm on the x-axis. As asphaltenes precipitated and were separated by the external centrifugal force toward the bottom of each centrifuge vial, the transmittance increased fairly uniformly throughout the length of the centrifuge vial. The untreated sample displayed a significant change in transmittance (FIG. 22) throughout the length of the centrifuge vial over the course of the test as destabilized asphaltenes were pulled to the bottom of the vial by the applied centrifugal force. FIGS. 23-24 illustrate measurable and rational changes in transmittance throughout the length of the sample vial over the course of the test for the treated samples. The ACSA method testing indicated improved asphaltene stability with increasing dosage of the asphaltene inhibitor going from 200 to 280 ppm. 280 ppm of asphaltene inhibitor decreased the instability index more than 50% over that obtained with 200 ppm. In contrast, the ASTM-type/Turbiscan™ method could not detect any significant difference between the samples with 200, 240, and 280 ppm asphaltene inhibitor.

As noted from FIGS. 18-25, the ACSA method performs better than the ASTM-type/Turbiscan™ method for discriminating between performances of the asphaltene inhibitors, even for relatively small changes in the chemical treatment dosage rate.

In the foregoing specification, the invention has been described with reference to specific embodiments thereof, and has been described as effective in providing methods for determining the stability of at least one foulant and/or relative efficacy of foulant inhibitor within a petroleum-based fluid sample. However, it will be evident that various modifications and changes can be made thereto without departing from the broader spirit or scope of the invention as set forth in the appended claims. Accordingly, the specification is to be regarded in an illustrative rather than a restrictive sense. For example, specific petroleum-based fluids, first components, second components, foulants, and foulant inhibitors falling within the claimed parameters, but not specifically identified or tried in a particular composition or method, are expected to be within the scope of this invention.

The present invention may suitably comprise, consist or consist essentially of the elements disclosed and may be practiced in the absence of an element not disclosed. For instance, the method may consist of or consist essentially of determining a stability of at least one foulant and/or petroleum-based fluid treated with foulant inhibitor within a petroleum-based fluid sample by centrifuging the petroleum-based fluid sample in a centrifuge vial having a petroleum-based fluid, at least one foulant, an optional additive for destabilizing the foulant, and an optional foulant inhibitor; the optional additive may include a first component selected from the group consisting of n-alkanes, iso-alkanes, alkenes, alkynes, cyclo-alkanes, natural gas, natural gas condensate, alcohols, ethers, ketones, organic acids, acetates, carbon dioxide, and combinations thereof; a light may be passed through the petroleum-based fluid sample to compare at least two identified amounts of transmitted light through the petroleum-based fluid sample at two or more time intervals and determine the stability of the foulant(s) and/or efficacy of foulant inhibitor(s).

The words "comprising" and "comprises" as used throughout the claims, are to be interpreted to mean "including but not limited to" and "includes but not limited to", respectively.

What is claimed is:

1. A method to determine a stability of at least one foulant within a petroleum-based fluid sample comprising:
    centrifuging a petroleum-based fluid sample in a centrifuge vial; wherein the petroleum-based fluid sample comprises at least one petroleum-based fluid and at least one foulant;
    passing a light through the petroleum-based fluid sample; and
    comparing at least two identified amounts of transmitted light at two or more time intervals through the petroleum-based fluid sample to determine the stability of the at least one foulant, wherein a change in transmittance indicates the stability of the at least one foulant.

2. The method of claim 1, wherein the petroleum-fluid based sample further comprises an effective amount of an additive for destabilizing the at least one foulant, wherein the additive comprises a first component selected from the group consisting of n-alkanes, iso-alkanes, alkenes, alkynes, cyclo-alkanes, natural gas, natural gas condensate, alcohols, ethers, ketones, organic acids, acetates, carbon dioxide, and combinations thereof.

3. The method of claim 2, wherein the number of carbons within the first component ranges from about 1 C to about 30 C.

4. The method of claim 2, wherein the amount of the additive within the petroleum-based fluid sample ranges from about 0.1 vol % to about 99 vol %.

5. The method of claim 4, further comprising adding the effective amount of the additive to the at least one petroleum-based fluid prior to centrifuging the petroleum-based fluid sample.

6. The method of claim 4, wherein the additive further comprises a second component selected from the group consisting of aromatic compounds, n-alkanes, iso-alkanes, alkenes, alkynes, cyclo-alkanes, natural gas, natural gas condensate, alcohols, ethers, ketones, organic acids, acetates, carbon dioxide, and combinations thereof.

7. The method of claim 1, wherein the at least one petroleum-based fluid is selected from the group consisting of a production fluid, crude oil, natural gas condensate, shale oil, shale gas condensate, bitumen, diluted bitumen (dil-bit), refinery fractions, finished fuel, finished petroleum products and combinations thereof.

8. The method of claim 1, wherein the centrifuging the petroleum-based fluid sample and the passing a light through the petroleum-based fluid sample occur at about the same time.

9. The method of claim 1, wherein an amount of the at least one petroleum-based fluid within the petroleum-based fluid sample ranges from about 1 vol % to about 100 vol %.

10. The method of claim 1, wherein the at least one foulant within the petroleum-based fluid sample ranges from about 0.1 wt % to about 30 wt %.

11. The method of claim 1, wherein the light source emits light having a wavelength ranging from about 370 nm to about 2500 nm.

12. The method of claim 1, wherein the centrifuge vial has a path length ranging from about 0.1 mm to about 15 mm.

13. The method of claim 1, wherein the at least one foulant is selected from the group consisting of asphaltenes, iron sulfide, waxes, coke, sand, ores, clays, hydrates, naphthenates, and combinations thereof.

14. The method of claim 1, wherein the petroleum-based fluid sample further comprises at least one foulant inhibitor.

15. A method comprising:
    centrifuging a petroleum-based fluid sample in a centrifuge vial; wherein the petroleum-based fluid sample comprises at least one petroleum-based fluid, at least one foulant, and an effective amount of an additive for destabilizing the at least one foulant; wherein the additive comprises a first component selected from the group consisting of n-alkanes, iso-alkanes, alkenes, alkynes, cyclo-alkanes, natural gas, natural gas condensate, alcohols, ethers, ketones, organic acids, acetates, carbon dioxide, and combinations thereof; wherein the at least one petroleum-based fluid is selected from the group consisting of a crude oil, a production fluid, natural gas condensate, shale oil, shale gas condensate, bitumen, diluted bitumen (dil-bit), refinery fractions, finished fuel, finished petroleum products, and combinations thereof;
    passing a light through the petroleum-based fluid sample, wherein the centrifuging the petroleum-based fluid sample and the passing a light through the petroleum-based fluid sample occur at about the same time; and
    comparing at least two identified amounts of transmitted light through the petroleum-based fluid sample at two or more time intervals to determine the stability of the at least one foulant, wherein a change in transmittance indicates the stability of the at least one foulant.

16. The method of claim 15, wherein an amount of the at least one petroleum-based fluid within the petroleum-based fluid sample ranges from about 1 vol % to about 99 vol %, and wherein the amount of the additive within the petroleum-based fluid sample ranges from about 1 vol % to about 99 vol %.

17. The method of claim 15, wherein the petroleum-based fluid sample further comprises at least one foulant inhibitor.

18. The method of claim 15 where the temperature of the petroleum-based fluid sample ranges from about 4 C to about 200 C.

19. A method for determining the efficacy of a foulant inhibitor in at least one petroleum-based fluid comprising:
    centrifuging a petroleum-based fluid sample in a centrifuge vial; wherein the petroleum-based fluid sample comprises at least one petroleum-based fluid, at least one foulant, at least one foulant inhibitor, and an effective amount of an additive for destabilizing the at least one foulant; wherein the at least one foulant is selected from the group consisting of asphaltenes, iron sulfide, waxes, coke, sand, ores, clays, hydrates, naphthenates, and combinations thereof; wherein the additive comprises a first component selected from the group consisting of n-alkanes, iso-alkanes, alkenes, alkynes, cyclo-alkanes, natural gas, natural gas condensate, alcohols, ethers, ketones, organic acids, acetates, carbon dioxide, and combinations thereof; wherein the amount of the at least one petroleum-based fluid within the petroleum-based fluid sample ranges from about 1 vol % to about 50 vol %;

passing a light through the petroleum-based fluid sample, wherein the centrifuging the petroleum-based fluid sample and the passing a light through the petroleum-based fluid sample occur at the same time; and comparing at least two identified amounts of transmitted light through the petroleum-based fluid sample at two or more time intervals to determine the stability of the at least one foulant, wherein a change in transmittance indicates the stability of the at least one foulant.

20. The method of claim 19, wherein the at least one petroleum-based fluid is selected from the group consisting of a crude oil, a production fluid, natural gas condensate, shale oil, shale gas condensate, bitumen, diluted bitumen (dil-bit), refinery fractions, finished fuel, finished petroleum products, and combinations thereof.

* * * * *